United States Patent [19]
Maienfisch et al.

[11] Patent Number: 5,763,481
[45] Date of Patent: Jun. 9, 1998

[54] VINYLCARBOXYLIC ACID DERIVATIVES

[75] Inventors: Peter Maienfisch, Rodersdorf, Switzerland; Manfred Böger, Weil am Rhein, Germany; Thomas Pitterna, Basel; Henry Szczepanski, Wallbach, both of Switzerland

[73] Assignee: Novartis Corproation, Summit, N.J.

[21] Appl. No.: 678,002

[22] Filed: Jul. 10, 1996

Related U.S. Application Data

[62] Division of Ser. No. 462,450, Jun. 5, 1995, Pat. No. 5,545,630, which is a continuation of Ser. No. 366,126, Dec. 29, 1994, abandoned.

[30] Foreign Application Priority Data

Dec. 29, 1993 [CH] Switzerland ............... 3895/93

[51] Int. Cl.$^6$ .................. A01N 37/22; C07C 233/12
[52] U.S. Cl. ............... 514/518; 514/535; 514/562; 514/567; 514/604; 514/616; 514/627; 554/42; 554/45; 554/51; 554/63; 554/67; 558/52; 560/47; 562/456; 564/86; 564/207; 564/155
[58] Field of Search ............... 564/207, 86, 155; 554/42, 45, 51, 63, 67; 560/47; 558/52; 562/456; 514/518, 535, 562, 567, 604, 616, 627

[56] References Cited

U.S. PATENT DOCUMENTS

| | | | |
|---|---|---|---|
| 3,996,254 | 12/1976 | Kühne | 556/419 |
| 4,950,666 | 8/1990 | Peake et al. | 514/227.5 |
| 5,081,287 | 1/1992 | Peake et al. | 560/219 |
| 5,248,810 | 9/1993 | Kohn et al. | 560/219 |
| 5,389,680 | 2/1995 | Ruminski | 514/563 |
| 5,457,134 | 10/1995 | Ruminski | 514/671 |
| 5,514,717 | 5/1996 | Phillion et al. | 514/601 |
| 5,561,162 | 10/1996 | Ruminski | 514/627 |
| 5,623,084 | 4/1997 | Ruminski | 558/54 |
| 5,627,174 | 5/1997 | Phillion et al. | 514/134 |

FOREIGN PATENT DOCUMENTS

| | | |
|---|---|---|
| 0432861 | 6/1991 | European Pat. Off. |
| 2507929 | 8/1975 | Germany |
| 9215555 | 9/1992 | WIPO |

OTHER PUBLICATIONS

Kraatz et al., Chemical Abstracts, vol. 126, abstract 238212, 1997.

*Primary Examiner*—Richard L. Raymond
*Attorney, Agent, or Firm*—William A. Teoli, Jr.; John D. Peabody, III

[57] ABSTRACT

Compounds of the formula $$\underset{X}{\overset{Y}{\underset{F}{>}}}\!\!=\!\!C\!-\!(CH_2)_m\!-\!\underset{\underset{R_{12}}{|}}{\overset{\overset{O}{\|}}{C}}\!-\!N\!-\!\text{Ar}(R_2)_n(R_1) \quad (I)$$

wherein
$R_1$ is $C_3$–$C_8$cycloalkyl, halo-$C_3$–$C_8$cycloalkyl, $C_3$–$C_8$cycloalkyl-$C_1$–$C_6$alkyl, halo-$C_3$–$C_8$cycloalkyl-$C_1$–$C_6$alkyl, —Si(R$_3$)$_3$, —S—R$_4$, —SO$_2$—R$_6$ or —CO—R$_9$;
$R_2$ is halogen, $C_1$–$C_4$alkyl or CF$_3$, the substituents $R_2$ being identical or different when n is 2;
$R_3$ each independently of the others is $C_1$–$C_6$alkyl, halo-$C_1$–$C_6$alkyl, $C_1$–$C_6$alkoxy or phenyl;
$R_4$ is aryl or heteroaryl each of which is unsubstituted or substituted;
$R_6$ is unsubstituted or substituted $C_1$–$C_{10}$alkyl, $C_2$–$C_6$alkenyl, $C_2$–$C_6$alkynyl, $C_1$–$C_{20}$-alkoxy, $C_2$–$C_6$alkenyloxy, $C_2$–$C_6$alkynyloxy, $C_1$–$C_4$alkylthio, aryl, aryloxy or arylthio, or is optionally substituted amino;
$R_9$ is hydroxy, unsubstituted or substituted $C_1$–$C_{10}$alkyl, $C_2$–$C_6$alkenyl, $C_2$–$C_6$alkynyl, $C_3$–$C_8$cycloalkyl, aryl or aryloxy, or is optionally substituted amino;
$R_{12}$ is hydrogen or unsubstituted or substituted $C_1$–$C_{10}$alkyl;
m is 1,3,5,7,9 or 11;
n is 0,1 or 2;
X is fluorine or chlorine; and
Y is hydrogen, fluorine or methyl; ps in free form or in salt form, can be used as pesticides and can be prepared in a manner known per se.

29 Claims, No Drawings

VINYLCARBOXYLIC ACID DERIVATIVES

This is a divisional of Ser. No. 08/462,450, filed Jun. 5, 1995, now U.S. Pat. No. 5,545,630 which is a continuation of Ser. No. 08/366,126, filed Dec. 29, 1994, now abandoned.

The invention relates to compounds of formula

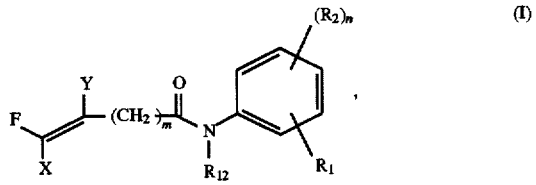

wherein $R_1$ is $C_3$–$C_8$cycloalkyl, halo-$C_3$–$C_8$cycloalkyl, $C_3$–$C_8$cycloalkyl-$C_1$–$C_6$alkyl, halo-$C_3$–$C_8$cycloalkyl-$C_1$–$C_6$alkyl, —Si($R_3$)$_3$, —S—$R_4$, —SO$_2$—$R_6$ or —CO—$R_9$;

$R_2$ is halogen, $C_1$–$C_4$alkyl or $CF_3$, the substituents $R_2$ being identical or different when n is 2;

$R_3$ each independently of the others is $C_1$–$C_6$alkyl, halo-$C_1$–$C_6$alkyl, $C_1$–$C_6$alkoxy or phenyl;

$R_4$ is aryl or heteroaryl each of which is unsubstituted or substituted;

$R_6$ is unsubstituted $C_1C_{10}$alkyl, $C_2$–$C_6$alkenyl, $C_2$–$C_6$alkynyl, $C_1$–$C_{20}$alkoxy, $C_2$–$C_6$alkenyloxy, $C_2$–$C_6$alkynyloxy, $C_1$–$C_4$alkylthio, aryl, aryloxy or arylthio, or substituted $C_1$–$C_{10}$alkyl, $C_2$–$C_6$alkenyl, $C_2$–$C_6$alkynyl, $C_1$–$C_{20}$alkoxy, $C_2$–$C_6$alkenyloxy, $C_2$–$C_6$alkynyloxy, $C_1$–$C_4$alkylthio, aryl, aryloxy or arylthio, or is —N($R_7$)$R_8$;

$R_7$ and $R_8$ are each independently of the other hydrogen, unsubstituted $C_1$–$C_{20}$alkyl, $C_2$–$C_6$alkenyl, $C_2$–$C_6$alkynyl, $C_3$–$C_8$cycloalkyl or aryl, or substituted $C_1$–$C_{20}$alkyl, $C_2$–$C_6$alkenyl, $C_2$–$C_6$alkynyl, $C_3$–$C_8$cycloalkyl or aryl; or $R_7$ and $R_8$ together form $C_4$–$C_6$alkylene, oxa-$C_3$–$C_5$alkylene or aza-$C_3$–$C_5$alkylene wherein the alkylene, oxaalkylene and azaalkylene groups are unsubstituted or substituted;

$R_9$ is hydroxy, unsubstituted $C_1$–$C_{10}$alkyl, $C_2$–$C_6$alkenyl, $C_2$–$C_6$alkynyl, $C_3$–$C_8$cycloalkyl, aryl or aryloxy, or substituted $C_1$–$C_{10}$alkyl, $C_2$–$C_6$alkenyl, $C_2$–$C_6$alkynyl, $C_3$–$C_8$cycloalkyl, aryl or aryloxy, or is —N($R_{10}$)$R_{11}$;

$R_{10}$ and $R_{11}$ are each independently of the other hydrogen, unsubstituted $C_1$–$C_{20}$alkyl, $C_2$–$C_6$alkenyl, $C_2$–$C_6$alkynyl, $C_3$–$C_8$cycloalkyl, aryl, pyridyl or quinolinyl, or substituted $C_1$–$C_{20}$alkyl, $C_2$–$C_6$alkenyl, $C_2$–$C_6$alkynyl, $C_3$–$C_8$cycloalkyl, aryl, pyridyl or quinolinyl, or $R_{10}$ and $R_{11}$ together form $C_4$–$C_6$alkylene, oxa-$C_3$–$C_5$-alkylene or aza-$C_3$–$C_5$alkylene wherein the alkylene, oxaalkylene and azaalkylene groups are unsubstituted or substituted;

$R_{12}$ is hydrogen or unsubstituted or substituted $C_1$–$C_{10}$-alkyl;

m is 1,3,5,7,9 or 11;

n is 0,1 or 2;

X is fluorine or chlorine; and

Y is hydrogen, fluorine or methyl;

in free form or in salt form, a process for the preparation of those compounds and the use of those compounds, pesticidal compositions comprising an active ingredient selected from those compounds, in free form or in agrochemically acceptable salt form, a process for the preparation of those compositions and the use of those compositions, plant propagation material treated with those compositions, a method of controlling pests, intermediates for the preparation of those compounds and a process for the preparation and the use of those intermediates.

In the literature, certain halovinylcarboxylic acid derivatives are proposed as active ingredients of pesticides. The biological properties of those known compounds are not entirely satisfactory in the field of pest control, however, and there is therefore a need to provide further compounds having pesticidal properties, especially for controlling insects and representatives of the order Acarina. That problem is solved according to the invention by the provision of the present compounds I.

Some of the compounds I can exist in the form of tautomers. If, for example, $R_{12}$ is hydrogen, then corresponding compounds I, i.e. those having a —(CH$_2$)$_m$—C(=O)—N(H)— part-structure, can exist in an equilibrium with the relevant tautomers, which have a —(CH$_2$)$_m$—C(OH)=N— part-structure. Accordingly, the compounds I hereinabove and hereinafter are, where appropriate, also to be understood as meaning corresponding tautomers, even when no specific mention is made of the latter in each individual case.

Compounds I which have at least one basic centre can form, for example, acid addition salts. These acid addition salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halogen-substituted, $C_1$–$C_4$alkanecarboxylic acids, for example acetic acid, or unsaturated or saturated dicarboxylic acids, for example oxalic acid, malonic acid, succinic acid, maleic acid, fumaric acid or phthalic acid, or hydroxycarboxylic acids, for example ascorbic acid, lactic acid, malic acid, tartaric acid or citric acid, or benzoic acid, or with organic sulfonic acids, such as unsubstituted or substituted, for example halogen-substituted, $C_1$–$C_4$alkane- or arylsulfonic acids, for example methane- or p-toluenesulfonic acid. Compounds I which have at least ore acidic group can furthermore form salts with bases. Suitable salts with bases are, for example, metal salts such as alkali metal salts or alkaline earth metal salts, for example sodium salts, potassium salts or magnesium salts, or salts with ammonia or with an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. Moreover, corresponding internal salts may also be formed, where possible. Preferred salts within the scope of the invention are agrochemically advantageous salts; however, the invention also comprises salts which are disadvantageous for agrochemical purposes, for example salts which are toxic to honey bees or fish and which are employed, for example, for isolating or purifying free compounds I or agrochemically utilisable salts thereof. Due to the close relationship between the compounds I in free form and in the form of the salts thereof, the free compounds I, or the salts thereof, are to be understood analogously hereinabove and hereinafter as meaning, if appropriate, also the corresponding salts and the free compounds I, respectively. The same applies to tautomers of compounds I and salts thereof. Generally preferred is, in each case, the free form.

The general terms used hereinabove and hereinbelow have the definitions given below unless defined otherwise.

A substituted cycloalkyl, aryl, heteroaryl, aryloxy, arylthio, pyridyl, quinolinyl, alkyl, alkoxy, alkylthio, alkylene, oxaalkylene, azaalkylene, alkenyl, alkynyl, alkenyloxy or alkynyloxy group can be mono- or polysubstituted, for example in the way given below.

Halogen—as a group per se and as a structural unit of other groups and compounds, such as of haloalkyl, haloalkylthio, halocycloalkyl, halocycloalkylalkyl, haloalkenyl, haloalkenyloxy, haloalkynyl, haloalkynyloxy, haloalkylenedioxy and haloalkoxy,—is fluorine, chlorine, bromine or iodine, especially fluorine, chlorine or bromine, more especially fluorine or chlorine, especially chlorine.

Unless defined otherwise, carbon-containing groups and compounds each contain from 1 up to and including 20, preferably from 1 up to and including 18, especially from 1 up to and including 10, more especially from 1 up to and including 6, very especially from 1 up to and including 4, more especially from 1 up to and including 3, especially 1 or 2, carbon atoms.

Cycloalkyl—as a group per se and as a structural unit of other groups and compounds, such as of cycloalkylalkyl, halocycloalkyl and halocycloalkylalkyl,—is cyclopropyl, cyclobutyl, cyclopentyl, cyclohexyl, cycloheptyl or cyclooctyl.

Alkyl—as a group per se and as a structural unit of other groups and compounds, such as of dialkylamino, cyanoalkyl, haloalkyl, cycloalkylalkyl, halocycloalkylalkyl, arylalkyl, pyridylalkyl, arylalkoxy, aryloxyalkyl, aryloxyalkoxy, alkoxy, alkoxyalkyl, alkoxyalkoxy, haloalkoxy, alkylcarbonyl, alkoxycarbonyl, alkoxycarbonyloxy, alkylthio), haloalkylthio, alkylsulfinyl, alkylsulfinyloxy, alkylsulfonyl and alkylsulfonyloxy,—in each case giving due consideration to the number of carbon atoms present in the group or compound in question—is either straight-chained, for example methyl, ethyl, n-propyl, n-butyl, n-hexyl, n-octyl, n-decyl, n-dodecyl, n-hexadecyl or n-octadecyl, or branched, for example isopropyl, isobutyl, sec-butyl, tert-butyl, isopentyl, neopentyl or isohexyl.

Alkylene is, for example, straight-chained, i. e. —(CH$_2$)—$_4$, —(CH$_2$) —$_5$ or —(C$_2$)—$_6$.

Oxaalkylene or azaalkylene contains, for example, one oxygen or nitrogen atom, is, for example, straight-chained and is, preferably, bonded via carbon atoms; examples are —CH$_2$—Q—CH$_2$—CH$_2$—, —CH$_2$—CH$_2$—Q—CH$_2$—CH$_2$—, —CH$_2$—CH$_2$—CH$_2$—Q—CH$_2$—, —CH$_2$—Q—CH$_2$—CH$_2$—CH$_2$—CH$_2$—and —CH$_2$—CH$_2$—Q—CH$_2$—CH$_2$—CH$_2$—, wherein Q is oxygen or nitrogen.

Alkylenedioxy—as a group per se and as a structural unit of other groups and compounds, such as of haloalkylenedioxy,—is methylenedioxy, ethylene-1,1-dioxy or ethylene,-1,2-dioxy.

Alkenyl and alkynyl—as groups per se and as structural units of other groups and compounds, such as of haloalkenyl, haloalkynyl, alkenyloxy, haloalkenyloxy, alkynyloxy and haloalkynyloxy,—are straight-chained or branched and each contain two or preferably one unsaturated carbon-carbon bond(s). The double or triple bonds of these substituents are preferably separated from the remaining part of the compound I by at least one saturated carbon atom. There may be mentioned by way of example vinyl, prop-2-en-1-yl, 2-methylprop-2-en-1-yl, but-2-en-1-yl, but-3-en-1-yl, prop-2-yn-1-yl, but-2-1-yl, and but-3-yn-1 -yl.

Halo-substituted carbon-containing groups and compounds, such as haloalkyl, halo-alkylthio, halocycloalkyl, halocycloalkylalkyl, haloalkenyl, haloalkenyloxy, haloalkynyl, haloalkynyloxy, haloalkylenedioxy and haloalkoxy, may be partially halogenated or perhalogenated, it being possible in the case of multiple halogenation for the halogen substituents to be identical or different. Examples of haloalkyl—as a group per se and as a structural unit of other groups and compounds, such as of haloalkylthio and haloalkoxy,—are methyl mono- to tri-substituted by fluorine, chlorine and/or by bromine, such as CHF$_2$, CF$_3$ or CH$_2$Cl; ethyl mono- to penta-substituted by fluorine, chlorine and/or by bromine, such as CH$_2$CF$_3$, CF$_2$CF$_3$, CF$_2$CCl$_3$, CF$_2$CHCl$_2$, CF$_2$CHF$_2$, CF$_2$CFCl$_2$, CH$_2$CH$_2$Cl, CF$_2$CHBr$_2$, CF$_2$CHClF, CF$_2$CHBrF or CClFCHClF; propyl or isopropyl mono- to hepta-substituted by fluorine, chlorine and/or by bromine, such as CH$_2$CHBrCH$_2$Br, CF$_2$CHFCF$_3$, CH$_2$CF$_2$CF$_3$, CF$_2$CF$_2$CF$_3$, CH(CF$_3$)$_2$ or CH$_2$CH$_2$CH$_2$Cl; and butyl mono- to nona-substituted by fluorine, chlorine and/or by bromine, or one of the isomers thereof, such as CF(CF$_3$)CHFCF$_3$, CF$_2$(CF$_2$)$_2$CF$_3$ or CH$_2$(CF$_2$)$_2$CF$_3$. Examples of haloalkenyl are 2,2-difluoroethen-1-yl, 2,2-dichloroethen-1-yl, 2-chloroprop-1-en-3-yl, 2,3-dichloroprop-1-en-3-yl and 2,3-dibromoprop-1-en-3-yl. Examples of haloalkenyloxy are 2,2-difluoroethen-1-yloxy, 2,2-dichloroethen-1-yloxy, 2-chloroprop-1-en-3-yloxy, 2,3-di- chloroprop-1-en-3-yloxy and 2,3-dibromoprop-1-en-3-yloxy. Examples of haloalkynyl are 3-chloroprop-1-yn-3-yl, 3,3-dichloroprop-1-yn-3-yl and 3,3-dibromoprop-1-yn-3-yl. Examples of haloalkynyloxy are 3-chloroprop-1-yn-3-yloxy, 3,3-dichloroprop-1-yn-3-yloxy and 3,3-dibromoprop-1-yn-3-yloxy. Examples of halocycloalkyl are 2-chlorocyclopropyl, 2,2-difluorocyclopropyl, 2-chloro-2-fluorocyclopropyl and 3,3-dichlorocyclohexyl. Examples of halocycloalkylalkyl are 2-chlorocyclopropylmethyl, 2,2-difluorocyclopropylmethyl and 3,3-dichlorocyclohexylmethyl. Examples of haloalkylenedioxy are difluoromethylenedioxy, dichloromethylenedioxy, 2,2,2-trichloroethylene-1,1-dioxy or 1,2-difluoroethylene-1,2-dioxy.

Aryl—as a group per se and as a structural unit of other groups and compounds, such as of aryloxy, arylthio, arylalkyl, arylalkoxy, aryloxyalkoxy and aryloxyalkyl,—is, for example, naphthyl or, preferably, phenyl.

Naphthyl—as a group per se and as a structural unit of other groups and compounds, such as of naphthoxy, naphthylthio and naphthylsulfonyl,—is naphth-1-yl or, preferably, naphth-2-yl.

Heteroryl is, for example, an aromatic, mono- or anellated bi-cyclic, heterocyclic radical, the ring(s) of this radical (each) being 5- or 6-membered, and this radical containing 1 to 3, preferably 1 or 2, ring hetero atoms, selected from the group consisting of nitrogen, oxygen and sulfur atoms. Preference is given to radicals having 1 or 2 ring nitrogen atoms, especially to pyridyl, preferably pyrid-2-yl, and pyrimidyl, preferably pyrimid-2-yl, radicals.

Pyridyl—as a group per se and as a structural unit of other groups and compounds, such as of pridyloxy and pyridylalkyl,—is pyrid-4-yl or, preferably, pyrid-2-yl or pyrid-3-yl.

Quinolinyl is quinolin-2-yl, quinolin-3-yl, quinolin-5-yl, quinolin-6-yl, quinolin-7-yl, quinolin-8-yl or, preferably, quinolin-4-yl.

In a halocycloalkylalkyl, arylalkyl, aryloxyalkyl, pyridylalkyl, cycloalkylalkyl, alkoxyalkyl or cyanoalkyl group, respectively, in each case an alkyl group bonded to the remainder of the compound I is substituted by 2 or 3 or, preferably, 1 halocycloalkyl, aryl, aryloxy, pyridyl, cycloalkyl, alkoxy or cyanoalkyl group(s), respectively.

In an arylalkoxy, aryloxyalkoxy or alkoxyalkoxy group, respectively, in each case an alkoxy group bonded to the remainder of the compound I is substituted by 2 or 3 or, preferably, 1 aryl, aryloxy or alkoxy group(s), respectively.

Preferred embodiments within the scope of the invention are:

(1) a compound of formula I, wherein
R$_1$ is C$_3$–C$_8$cycloalkyl, halo-C$_3$–C$_8$cycloalkyl, C$_3$–C$_8$cycloalkyl-C$_1$–C$_6$alkyl, halo-C$_3$–C$_8$cycloalkyl-C$_1$–C$_6$alkyl, —Si(R$_3$)$_3$, —S—R$_4$, —SO$_2$—R$_6$ or —CO—R$_9$;

$R_2$ is halogen, methyl or $CF_3$, the substituents $R_2$ being identical or different when n is 2;

$R_3$ each independently of the others is $C_1$–$C_6$alkyl, halo-$C_1$–$C_6$alkyl, $C_1$–$C_6$alkoxy or phenyl;

$R_4$ is aryl or heteroaryl each of which is unsubstituted or substituted;

$R_6$ is unsubstituted $C_1$–$C_{10}$alkyl, $C_2$–$C_6$alkenyl, $C_1$–$C_6$alkoxy, $C_3$–$C_6$alkenyloxy, $C_3$–$C_6$alkynyloxy, $C_1$–$C_4$alkylthio, aryl, aryloxy or arylthio, or substituted $C_1$–$C_{10}$-alkyl, $C_2$–$C_6$alkenyl, $C_1$–$C_6$alkoxy, $C_3$–$C_6$alkenyloxy, $C_3$–$C_6$alkynyloxy, $C_1$–$C_4$-alkylthio, aryl, aryloxy or arylthio, or is —$N(R_7)R_8$;

$R_7$ and $R_8$ are each independently of the other hydrogen, unsubstituted $C_1$–$C_{20}$alkyl, $C_2$–$C_6$alkenyl, $C_2$–$C_6$alkynyl, $C_3$–$C_8$cycloalkyl or aryl, or substituted $C_1$–$C_{20}$alkyl, $C_2$–$C_6$alkenyl, $C_2$–$C_6$alkynyl, $C_3$–$C_8$cycloalkyl or aryl; or together form $C_4$–$C_6$-alkylene, oxa-$C_3$–$C_5$alkylene or aza-$C_3$–$C_5$alkylene wherein the alkylene, oxa-alkylene and azaalkylene groups are unsubstituted or substituted;

$R_9$ is hydroxy, unsubstituted $C_1$–$C_{10}$alkyl, $C_3$–$C_6$alkenyl, $C_3$–$C_6$alkynyl, $C_3$–$C_8$cycloalkyl, aryl or aryloxy, or substituted $C_1$–$C_{10}$alkyl, $C_3$–$C_6$alkenyl, $C_3$–$C_6$alkynyl, $C_3$–$C_8$cycloalkyl, aryl or aryloxy, or is —$N(R_{10})R_{11}$;

$R_{10}$ and $R_{11}$ are each independently of the other hydrogen, unsubstituted $C_1$–$C_{10}$alkyl, $C_3$–$C_6$alkenyl, $C_3$–$C_6$alkynyl, $C_3$–$C_8$cycloalkyl, aryl or pyridyl, or substituted $C_1$–$C_{10}$alkyl, $C_3$–$C_6$alkenyl, $C_3$–$C_6$alkynyl, $C_3$–$C_8$cycloalkyl, aryl or pyridyl, or together form $C_4$–$C_6$alkylene, oxa-$C_3$–$C_5$alkylene or aza-$C_3$–$C_5$alkylene wherein the alkylene, oxaalkylene and azaalkylene groups are unsubstituted or substituted;

$R_{12}$ is hydrogen;

m is 1,3,5,7,9 or 11;

n is 0, 1 or 2;

X is fluorine or chlorine; and

Y is hydrogen, fluorine or methyl.

(2) a compound of formula I, wherein $R_1$ is $C_3$–$C_8$cycloalkyl, halo-$C_3$–$C_8$cycloalkyl, $C_3$–$C_8$cycloalkyl-$C_1$–$C_6$alkyl, halo-$C_3$–$C_8$-cycloalkyl-$C_1$–$C_6$alkyl, —$Si(R_3)_3$, -S—$R_4$, —$SO_2$—$R_6$ or —CO—$R_9$;

$R_3$ each independently of the others is $C_1$–$C_6$alkyl, halo-$C_1$–$C_6$alkyl, $C_1$–$C_6$alkoxy or phenyl;

$R_4$ is aryl or heteroaryl each of which is unsubstituted or substituted;

$R_6$ is unsubstituted $C_1$–$C_{10}$alkyl, $C_2$–$C_6$alkenyl, $C_2$–$C_6$alkynyl, $C_1$–$C_{20}$alkoxy, $C_2$–$C_6$-alkenyloxy, $C_2$–$C_6$alkynyloxy, $C_1$–$C_4$alkylthio, aryl, aryloxy or arylthio, or substituted $C_1$–$C_{10}$alkyl, $C_2$–$C_6$alkenyl, $C_2$–$C_6$alkynyl, $C_1$–$C_{20}$alkoxy, $C_2$–$C_6$-alkenyloxy, $C_2$–$C_6$alkynyloxy, $C_1$–$C_4$alkylthio, aryl, aryloxy or arylthio, or is —$N(R_7)R_8$;

$R_7$ and $R_8$ are each independently of the other hydrogen, unsubstituted $C_1$–$C_{20}$alkyl, $C_2$–$C_6$alkenyl, $C_2$–$C_6$alkynyl, $C_3$–$C_8$cycloalkyl or aryl, or substituted $C_1$–$C_{20}$alkyl, $C_2$–$C_6$alkenyl, $C_2$–$C_6$alkynyl, $C_3$–$C_8$cycloalkyl or aryl; or $R_7$ and $R_8$ together form $C_4$–$C_6$alkylene, oxa-$C_3$–$C_5$alkylene or aza-$C_3$–$C_5$alkylene wherein the alkylene, oxaalkylene and azaalkylene groups are unsubstituted or substituted;

$R_9$ is hydroxy, unsubstituted $C_1$–$C_{10}$alkyl, $C_2$–$C_6$alkenyl, $C_2$–$C_6$alkynyl, $C_3$–$C_8$cycloalkyl, aryl or aryloxy, or substituted $C_1$–$C_{10}$alkyl, $C_2$–$C_6$alkenyl, $C_2$–$C_6$alkynyl, $C_3$–$C_8$cycloalkyl, aryl or aryloxy, or is —$N(R_{10})R_{11}$; and $R_{10}$ and $R_{11}$ are each independently of the other hydrogen, unsubstituted $C_1$–$C_{20}$alkyl, $C_2$–$C_6$alkenyl, $C_2$–$C_6$alkynyl, $C_3$–$C_8$cycloalkyl, aryl, pyridyl or quinolinyl, or substituted $C_1$–$C_{20}$alkyl, $C_2$–$C_6$alkenyl, $C_2$–$C_6$alkynyl, $C_3$–$C_8$cycloalkyl, aryl, pyridyl or quinolinyl, or $R_{10}$ and $R_{11}$ together form $C_4$–$C_6$alkylene, oxa-$C_3$–$C_5$-alkylene or aza-$C_3$–$C_5$alkylene wherein the alkylene, oxaalkylene and azaalkylene groups are unsubstituted or substituted;

especially $R_1$ is $C_3$–$C_8$cycloalkyl, halo-$C_3$–$C_8$cycloalkyl, $C_3$–$C_8$cycloalkyl-$C_1$–$C_6$alkyl, halo-$C_3$–$C_8$cycloalkyl-$C_1$–$C_6$alkyl, —$Si(R_3)_3$, —S—$R_4$, —$SO_2$—$R_6$ or —CO—$R_9$;

$R_3$ each independently of the others is $C_1$–$C_6$alkyl, halo-$C_1$–$C_6$alkyl, $C_1$–$C_6$alkoxy or phenyl;

$R_4$ is aryl which is unsubstituted or substituted by from one to three substituents, selected from the group consisting of halogen, $C_1$–$C_{10}$alkyl, $C_2$–$C_6$alkenyl, $C_2$–$C_6$alkynyl, $C_3$–$C_8$cycloalkyl, halo-$C_1$–$C_6$alkyl, halo-$C_2$–$C_6$alkenyl, halo-$C_2$–$C_6$alkynyl, $C_1$–$C_6$alkoxy, $C_2$–$C_6$alkenyloxy, $C_2$–$C_6$alkynyloxy, halo-$C_1$–$C_6$alkoxy, halo-$C_2$–$C_6$alkenyloxy, halo-$C_2$–$C_6$alkynyloxy, $C_1$–$C_6$alkylthio, halo-$C_1$–$C_{10}$alkylthio, $C_1$–$C_6$alkoxy-$C_1$–$C_6$alkyl, $C_1$–$C_4$alkylsulfinyl, $C_1$–$C_4$alkylsulfonyl, $C_1$–$C_4$alkylsulfinyloxy, $C_1$–$C_4$alkylsulfonyloxy, di-$C_1$–$C_6$alkylamino wherein the alkyl radicals are the same or different, —C(=O)—$R_5$, nitro, $C_1$–$C_2$alkylendioxy, halo-$C_1$–$C_2$alkylendioxy, cyano, and a phenyl, naphthyl, phenoxy, naphthoxy, phenylthio, naphthylthio, phenylsulfonyl, naphthylsulfonyl or pyridyloxy group, which is unsubstituted or mono- or di-substituted by substituents being selected from the group consisting of halogen, $C_1$–$C_4$alkyl and halo-$C_1$–$C_4$alkyl; or $R_4$ is heteroaryl which is unsubstituted or substituted by from one to three substituents, selected from the group consisting of halogen, nitro, $C_1$–$C_4$alkyl, $C_2$–$C_6$alkenyl, $C_2$–$C_6$alkynyl, halo-$C_2$–$C_6$alkenyl, halo-$C_2$–$C_6$alkynyl, $C_3$–$C_8$cycloalkyl, halo-$C_1$–$C_4$alkyl, $C_1$–$C_4$alkoxy, $C_2$–$C_6$alkenyloxy, $C_2$–$C_6$alkynyloxy, halo-$C_1$–$C_4$alkoxy,halo-$C_2$–$C_6$alkenyloxy, halo-$C_2$–$C_6$alkynyloxy, $C_1$–$C_4$alkylthio, halo-$C_1$–$C_4$alkylthio, $C_1$–$C_4$alkylsulfinyl, $C_1$–$C_4$alkylsulfonyl, $C_1$–$C_4$alkylsulfinyloxy, $C_1$–$C_4$alkylsulfonyloxy, $C_1$–$C_4$alkylcarbonyl, $C_1$–$C_4$alkoxycarbonyl and cyano;

$R_5$ is $C_1$–$C_{10}$alkyl, halo-$C_1$–$C_6$alkyl, $C_1$–$C_6$alkoxy, halo-$C_1$–$C_6$alkoxy, $C_3$–$C_6$cycloalkyl, halo-$C_3$–$C_6$cycloalkyl, $C_3$–$C_6$cycloalkyl-$C_1$–$C_3$alkyl or halo-$C_3$–$C_6$cycloalkyl-$C_1$–$C_3$-alkyl;

$R_6$ is $C_1$–$C_{10}$alkyl, $C_2$–$C_6$alkenyl, $C_2$–$C_6$alkynyl, halo-$C_1$–$C_6$alkyl, halo-$C_2$–$C_6$alkenyl, halo-$C_2$–$C_6$alkynyl, $C_1$–$C_{20}$alkoxy, halo-$C_1$–$C_6$alkoxy, $C_1$–$C_6$alkoxy-$C_1$–$C_6$alkyl, $C_1$–$C_6$alkoxy-$C_1$–$C_6$alkoxy, $C_2$–$C_6$alkenyloxy, halo-$C_2$–$C_6$alkenyloxy, $C_2$–$C_6$alkynyloxy, halo-$C_2$–$C_6$alkynyloxy, $C_1$–$C_4$alkylthio, halo-$C_1$–$C_{10}$alkylthio, —$N(R_7)R_8$, or an aryl, aryloxy, aryl-$C_1$–$C_6$alkyl, aryl-$C_1$–$C_6$alkoxy, aryloxy-$C_1$–$C_6$alkoxy, arylthio or aryloxy-$C_1$–$C_6$alkyl group, wherein the aryl radical is unsubstituted or mono-, di- or tri-substituted, substituents being selected from the group consisting of halogen, $C_1-C_4$alkyl, nitro, cyano, $C_1-C_4$alkoxy, phenoxy and halo-$C_1-C_4$alkyl;

$R_7$ and $R_8$ are each independently of the other hydrogen, $C_1-C_{20}$alkyl, $C_2-C_6$alkenyl, $C_2-C_6$alkynyl, halo-$C_1-C_{10}$alkyl, halo-$C_2-C_6$alkenyl, halo-$C_2-C_6$alkynyl, $C_3-C_8$-cycloalkyl, halo-$C_3-C_8$cycloalkyl, $C_3-C_8$cycloalkyl-$C_1-C_6$alkyl, $C_1-C_6$alkoxy-$C_1-C_{10}$alkyl, cyano-$C_1-C_6$alkyl, or an aryl, aryl-$C_1-C_6$alkyl or aryloxy-$C_1-C_6$alkyl group, wherein the aryl radical is unsubstituted or substituted by from one to three substituents, selected from the group consisting of halogen, $C_1-C_4$alkyl, nitro, cyano, $C_1-C_4$alkoxy, phenoxy, $C_1-C_6$alkylcarbonyloxy, halo-$C_1-C_4$alkyl and halo-$C_1-C_4$alkoxy; or $R_7$ and $R_8$ together form a straight-chained $C_4-C_6$alkylene group, a straight-chained oxa-$C_3-C_5$alkylene group bonded via carbon, or a straight-chained aza-$C_3-C_5$alkylene group bonded via carbon, the alkylene, oxaalkylene or azaalkylene group being unsubstituted or mono- or di-substituted by methyl;

$R_9$ is hydroxy, $C_1-C_{10}$alkyl, halo-$C_1-C_{10}$alkyl, $C_1-C_6$alkoxy-$C_1-C_6$alkyl, $C_2-C_6$alkenyl, $C_2-C_6$alkynyl, halo-$C_2-C_6$alkenyl, halo-$C_2-C_6$alkynyl, $C_3-C_8$cycloalkyl, $C_3-C_8$cycloalkyl-$C_1-C_6$alkyl, halo-$C_3-C_8$cycloalkyl, $-N(R_{10})R_{11}$, or an aryl, aryloxy, aryl-$C_1-C_6$-alkyl or aryloxy-$C_1-C_4$alkyl group, wherein the aryl radical is unsubstituted or substituted by from one to three substituents, selected from the group consisting of halogen, $C_1-C_4$alkyl, halo-$C_1-C_4$alkyl, nitro, cyano and $C_1-C_4$alkoxy; and $R_{10}$ and $R_{11}$ are each independently of the other hydrogen, $C_1-C_{20}$alkyl, $C_2-C_6$alkenyl, $C_2-C_6$alkynyl, halo-$C_1-C_{10}$alkyl, halo-$C_2-C_6$alkenyl, halo-$C_2-C_6$alkenyl, $C_3-C_8$cycloalkyl, halo-$C_3-C_8$cycloalkyl, halo-$C_3-C_8$cycloalkyl-$C_1-C_6$alkyl, $C_3-C_8$-cycloalkyl-$C_1-C_6$alkyl, $C_1-C_6$alkoxy-$C_1-C_6$alkyl, or an aryl, pyridyl, quinolinyl, aryl-$C_1-C_6$alkyl or pyridyl-$C_1-C_6$alkyl group, which is unsubstituted or ring-substituted by from one to three substituents, selected from the group consisting of halogen, $C_1-C_4$alkyl, halo-$C_1-C_4$alkyl, nitro, cyano, $C_1-C_4$alkoxy, halo-$C_1-C_4$alkoxy and phenoxy; or $R_{10}$ and $R_{11}$ together form a straight-chained $C_4-C_6$alkylene group, a straight-chained oxa-$C_3-C_5$alkylene group bonded via carbon, or a straight-chained aza-$C_3-C_5$alkylene group bonded via carbon, the alkylene, oxaalkylene or azaalkylene group being unsubstituted or mono- or di-substituted by methyl, (3) a compound of formula I, wherein $R_1$ is $-Si(R_3)_3$ and $R_3$ each independently of the others is $C_1-C_6$alkyl, halo-$C_1-C_6$alkyl, $C_1-C_6$alkoxy or phenyl;

especially $R_1$ is $-Si(R_3)_3$ and $R_3$ each independently of the others is $C_1-C_4$alkyl or $C_1-C_4$alkoxy;

more especially $R_1$ is $-Si(R_3)_3$ and $R_3$ each independently of the others is $C_1-C_4$alkyl;

more especially $R_1$ is $-Si(R_3)_3$ and each $R_3$ is the same $C_1-C_4$alkyl;

more especially $R_1$ is $-Si(R_3)_3$ and each $R_3$ is methyl, (4) a compound of formula I, wherein $R_1$ is $-S-R_4$ and $R_4$ is aryl or heteroaryl each of which is unsubstituted or substituted;

especially $R_1$ is $-S-R_4$ and $R_4$ is aryl which is unsubstituted or substituted by from one to three substituents, selected from the group consisting of halogen, $C_1-C_{10}$alkyl, $C_2-C_6$alkenyl, $C_2-C_6$alkynyl, $C_3-C_8$cycloalkyl, halo-$C_1-C_6$alkyl, halo-$C_2-C_6$alkenyl, halo-$C_2-C_6$alkynyl, $C_1-C_6$alkoxy, $C_2-C_6$alkenyloxy, $C_2-C_6$alkynyloxy, halo-$C_1-C_6$alkoxy, halo-$C_2-C_6$alkenyloxy, halo-$C_2-C_6$alkynyloxy, $C_1-C_6$alkylthio, halo-$C_1-C_{10}$alkylthio, $C_1-C_6$alkoxy-$C_1-C_6$alkyl, $C_1-C_4$alkylsulfinyl, $C_1-C_4$alkylsulfonyl, $C_1-C_4$alkylsulfinyloxy, $C_1-C_4$alkylsulfonyloxy, di-$C_1-C_6$alkylamino wherein the alkyl radicals are the same or different, $-C(=O)-R_5$, nitro, $C_1-C_2$alkylendioxy, halo-$C_1-C_2$alkylendioxy, cyano, and a phenyl, naphthyl, phenoxy, naphthoxy, phenylthio, naphthylthio, phenylsulfonyl, naphthylsulfonyl or pyridyloxy group, which is unsubstituted or mono- or di-substituted by substituents being selected from the group consisting of halogen, $C_1-C_4$alkyl and halo-$C_1-C_4$alkyl, or $R_4$ is heteroaryl which is unsubstituted or substituted by from one to three substituents, selected from the group consisting of halogen, nitro, $C_1-C_4$alkyl, $C_2-C_6$alkenyl, $C_2-C_6$alkynyl, halo-$C_2-C_6$alkenyl, halo-$C_2-C_6$alkynyl, $C_3-C_8$cycloalkyl, halo-$C_1-C_4$alkyl, $C_1-C_4$alkoxy, $C_2-C_6$alkenyloxy, $C_2-C_6$alkynyloxy, halo-$C_1-C_4$alkoxy, halo-$C_2-C_6$alkenyloxy, halo-$C_2-C_6$alkynyloxy, $C_1-C_4$alkylthio, halo-$C_1-C_4$alkylthio, $C_1-C_4$alkylsulfinyl, $C_1-C_4$alkylsulfonyl, $C_1-C_4$alkylsulfinyloxy, $C_1-C_4$alkylsulfonyloxy, $C_1-C_4$alkylcarbonyl, $C_1-C_4$alkoxycarbonyl and cyano, and $R_5$ is $C_1-C_{10}$alkyl, halo-$C_1-C_6$alkyl, $C_1-C_6$alkoxy, halo-$C_1-C_6$alkoxy, $C_3-C_6$cycloalkyl, halo-$C_3-C_6$cycloalkyl, $C_3-C_6$cycloalkyl-$C_1-C_3$alkyl or halo-$C_3-C_6$cycloalkyl-$C_1-C_3$alkyl;

more especially $R_1$ is $-S-R_4$ and $R_4$ is aryl which is unsubstituted or substituted by from one to three substituents, selected from the group consisting of halogen, $C_1-C_{10}$alkyl, $C_2-C_6$alkenyl, $C_2-C_6$alkynyl, $C_3-C_8$cycloalkyl, halo-$C_1-C_6$alkyl, halo-$C_2-C_6$alkenyl, halo-$C_2-C_6$alkynyl, $C_1-C_6$alkoxy, $C_2-C_6$alkenyloxy, $C_2-C_6$alkynyloxy, halo-$C_1-C_6$alkoxy, halo-$C_2-C_6$alkenyloxy, halo-$C_2-C_6$alkynyloxy, $C_1-C_6$alkylthio, halo-$C_1-C_{10}$alkylthio, $C_1-C_6$alkoxy-$C_1-C_6$alkyl, $C_1-C_4$alkylsulfinyl, $C_1-C_4$alkylsulfonyl, $C_1-C_4$alkylsulfinyloxy, $C_1-C_4$alkylsulfonyloxy, di-$C_1-C_6$alkylamino wherein the alkyl radicals are the same or different, $-C(=O)-R_5$, nitro, $C_1-C_2$alkylendioxy, halo-$C_1-C_2$alkylendioxy, cyano, and a phenyl, naphthyl, phenoxy, naphthoxy, phenylthio, naphthylthio, phenylsulfonyl, naphthylsulfonyl or pyridyloxy group, which is unsubstituted or mono- or di-substituted by substituents being selected from the group consisting of halogen, $C_1-C_4$alkyl and halo-$C_1-C_4$alkyl, and $R_5$ is $C_1-C_{10}$alkyl, halo-$C_1-C_6$alkyl, $C_1-C_6$alkoxy, halo-$C_1-C_6$alkoxy, $C_3-C_6$cycloalkyl, halo-$C_3-C_6$cycloalkyl, $C_3-C_6$cycloalkyl-$C_1-C_3$alkyl or halo-$C_3C_6$cycloalkyl-$C_1-C_3$alkyl;

more especially $R_1$ is $-S-R_4$ and $R_4$ is aryl that is unsubstituted or substituted by one to three substituents, selected from the group consisting of halogen, $C_1$–$C_6$alkyl, $C_5$–$C_8$cycloalkyl and $C_1$–$C_4$alkoxy;

preferably $R_1$ is —S—$R_4$ and $R_4$ is a phenyl or naphthyl group, which is unsubstituted or substituted by one or two substituents, selected from the group consisting of halogen and $C_1$–$C_4$alkyl;

more preferably $R_1$ is —S—$R_4$ and $R_4$ is unsubstituted naphthyl or phenyl, which is unsubstituted or monosubstituted by halogen or by methyl, (5) a compound of formula I, wherein $R_1$ is —S—$R_4$ and $R_4$ is heteroaryl, which is unsubstituted or substituted by from one to three substituents, selected from the group consisting of halogen, nitro, $C_1$–$C_4$alkyl, $C_2$–$C_6$alkenyl, $C_2$–$C_6$alkynyl, halo-$C_2$–$C_6$alkenyl, halo-$C_2$–$C_6$alkynyl, $C_3$–$C_8$cycloalkyl, halo-$C_1$–$C_4$alkyl, $C_1$–$C_4$alkoxy, $C_2$–$C_6$alkenyloxy, $C_2$–$C_6$alkynyloxy, halo-$C_1$–$C_4$alkoxy, halo-$C_2$–$C_6$alkenyloxy, halo-$C_2$–$C_6$alkynyloxy, $C_1$–$C_4$alkylthio, halo-$C_1$–$C_4$alkylthio, $C_1$–$C_4$alkylsulfinyl, $C_1$–$C_4$alkylsulfonyl, $C_1$–$C_4$alkylsulfinyloxy, $C_1$–$C_4$alkylsulfonyloxy, $C_1$–$C_4$alkylcarbonyl, $C_1$–$C_4$alkoxycarbonyl and cyano;

especially $R_1$ is —S—$R_4$ and $R_4$ is heteroaryl having 1 or 2 ring nitrogen atoms, which is unsubstituted or substituted by one or two substituents, selected from the group consisting of halogen, halo-$C_1$–$C_4$alkyl and nitro;

more especially $R_1$ is —S—$R_4$ and $R_4$ is a pyridyl or pyrimidyl group, which is unsubstituted or substituted by one or two substituents, selected from the group consisting of halogen, halo-$C_1$–$C_4$alkyl and nitro;

more especially $R_1$ is —S—$R_4$ and $R_4$ is a pyrid-2-yl or pyrimid-2-yl group, which is unsubstituted or mono-substituted by halogen, $CF_3$ or nitro, (6) a compound of formula I, wherein $R_1$ is —$SO_2$—$R_6$ and $R_6$ is unsubstituted $C_1$–$C_{10}$alkyl, $C_2$–$C_6$alkenyl, $C_2$–$C_6$alkynyl, $C_1$–$C_{20}$alkoxy, $C_2$–$C_6$alkenyloxy, $C_2$–$C_6$alkynyloxy, $C_1$–$C_4$alkylthio, aryl, aryloxy or arylthio, or substituted $C_1$–$C_{10}$alkyl, $C_2$–$C_6$alkenyl, $C_2$–$C_6$alkynyl, $C_1$–$C_{20}$alkoxy, $C_2$–$C_6$alkenyloxy, $C_2$–$C_6$alkynyloxy, $C_1$–$C_4$alkylthio, aryl, aryloxy or arylthio, or is —N($R_7$)$R_8$ and $R_7$ and $R_8$ are each independently of the other hydrogen, unsubstituted $C_1$–$C_{20}$alkyl, $C_2$–$C_6$alkenyl, $C_2$–$C_6$alkynyl, $C_3$–$C_8$cycloalkyl or aryl, or substituted $C_1$–$C_{20}$alkyl, $C_2$–$C_6$alkenyl, $C_2$–$C_6$-alkynyl, $C_3$–$C_8$cycloalkyl or aryl or $R_7$ and $R_8$ together form $C_4$–$C_6$alkylene, oxa-$C_3$–$C_5$alkylene or aza-$C_3$–$C_5$alkylene wherein the alkylene, oxaalkylene and azaalkylene groups are unsubstituted or substituted;

especially $R_1$ is —$SO_2$—$R_6$ and $R_6$ is $C_1$–$C_{10}$alkyl, $C_2$–$C_6$alkenyl, $C_2$–$C_6$alkynyl, halo-$C_1$–$C_6$alkyl, halo-$C_2$–$C_6$alkenyl, halo-$C_2$–$C_6$alkynyl, $C_1$–$C_{20}$alkoxy, halo-$C_1$–$C_6$alkoxy, $C_1$–$C_6$alkoxy-$C_1$–$C_6$alkyl, $C_1$–$C_6$alkoxy-$C_1$–$C_6$alkoxy, $C_2$–$C_6$alkenyloxy, halo-$C_2$–$C_6$alkenyloxy, $C_2$–$C_6$alkynyloxy, halo-$C_2$–$C_6$alkynyloxy, $C_1$–$C_4$alkylthio., halo-$C_1$–$C_{10}$alkylthio, —N($R_7$)$R_8$, or an aryl, aryloxy, aryl-$C_1$–$C_6$alkyl, aryl-$C_1$–$C_6$alkoxy, aryloxy-$C_1$–$C_6$alkoxy, arylthio or aryloxy-$C_1$–$C_6$alkyl group, wherein the aryl radical is unsubstituted or mono-, di- or tri-substituted, substituents being selected from the group consisting of halogen, $C_1$–$C_4$alkyl, nitro, cyano, $C_1$–$C_4$alkoxy, phenoxy and halo-$C_1$–$C_4$alkyl, and $R_7$ and $R_8$ are each independently of the other hydrogen, $C_1$–$C_{20}$alkyl, $C_2$–$C_6$alkenyl, $C_2$–$C_6$alkynyl, halo-$C_1$–$C_{10}$alkyl, halo-$C_2$–$C_6$alkenyl, halo-$C_2$–$C_6$alkynyl, $C_3$–$C_8$cycloalkyl, halo-$C_3$–$C_8$cycloalkyl, $C_3$–$C_8$cycloalkyl-$C_1$–$C_6$alkyl, $C_1$–$C_6$alkoxy $C_1$–$C_{10}$alkyl, cyano-$C_1$–$C_6$alkyl, or an aryl, aryl-$C_1$–$C_6$alkyl or aryloxy-$C_1$–$C_6$alkyl group, wherein the aryl radical is unsubstituted or substituted by from one to three substituents, selected from the group consisting of halogen, $C_1$–$C_4$alkyl, nitro, cyano, $C_1$–$C_4$alkoxy, phenoxy, $C_1$–$C_6$alkylcarbonyloxy, halo-$C_1$–$C_4$alkyl and halo-$C_1$–$C_4$alkoxy, or $R_7$ and $R_8$ together form a straight-chained $C_4$–$C_6$alkylene group, a straight-chained oxa-$C_3$–$C_5$alkylene group bonded via carbon, or a straight-chained aza-$C_3$–$C_5$alkylene group bonded via carbon, the alkylene, oxaalkylene or azaalkylene group being unsubstituted or mono-or di-substituted by methyl;

more especially $R_1$ is —$SO_2$—$R_6$ and $R_6$ is unsubstituted $C_1$–$C_{10}$alkyl, $C_2$–$C_6$alkenyl, $C_2$–$C_6$-alkynyl, $C_1$–$C_{20}$alkoxy, $C_2$–$C_6$alkenyloxy, $C_2$–$C_6$alkynyloxy, $C_1C_4$alkylthio, aryl, aryloxy or arylthio, or substituted $C_1$–$C_{10}$alkyl, $C_2$–$C_6$alkenyl, $C_2$–$C_6$alkynyl, $C_1$–$C_{20}$alkoxy, $C_2$–$C_6$-alkenyloxy, $C_2$–$C_6$alkynyloxy, $C_1$–$C_4$alkylthio, aryl, aryloxy or arylthio; more especially $R_1$ is —$SO_2$—$R_6$ and $R_6$ is $C_1$–$C_{10}$alkyl, $C_2$–$C_6$alkenyl, $C_2$–$C_6$alkynyl, halo-$C_1$–$C_6$alkyl, halo-$C_2$–$C_6$alkenyl, halo-$C_2$–$C_6$alkynyl, $C_1$–$C_{20}$alkoxy, halo-$C_1$–$C_6$alkoxy, $C_1$–$C_6$alkoxy-$C_1$–$C_6$alkyl, $C_1$–$C_6$alkoxy-$C_1$–$C_6$alkoxy, $C_2$–$C_6$alkenyloxy, halo-$C_2$–$C_6$alkenyloxy, $C_2$–$C_6$alkynyloxy, halo-$C_2$–$C_6$alkynyloxy, $C_1$–$C_4$alkylthio, halo-$C_1$–$C_{10}$alkylthio, or an aryl, aryloxy, aryl-$C_1$–$C_6$alkyl, aryl-$C_1$–$C_6$alkoxy, aryloxy-$C_1$–$C_6$alkoxy, arylthio or aryloxy-$C_1$–$C_6$alkyl group, wherein the aryl radical is unsubstituted or mono-, di- or tri-substituted, substituents being selected from the group consisting of halogen, $C_1$–$C_4$alkyl, nitro, cyano, $C_1$–$C_4$alkoxy, phenoxy and halo-$C_1$–$C_4$alkyl;

more especially $R_1$ is —$SO_2$—$R_6$ and $R_6$ is $C_1$–$C_6$alkyl, $C_1$–$C_{20}$alkoxy, $C_1$–$C_4$alkoxy or an aryl-$C_1$–$C_4$alkoxy, aryloxy-$C_1$–$C_4$alkoxy, aryl or aryloxy group, in which the aryl group is unsubstituted;

more especially $R_1$ is —$SO_2$—$R_6$ and $R_6$ is $C_1$–$C_6$alkyl, (7) a compound of formula I, wherein $R_1$ is —$SO_2$—$R_6$, $R_6$ is —N($R_7$)$R_8$ and $R_7$ and $R_8$ are each independently of the other hydrogen, unsubstituted $C_1$–$C_{20}$alkyl, $C_2$–$C_6$alkenyl, $C_2$–$C_6$alkynyl, $C_3$–$C_8$cycloalkyl or aryl, or substituted $C_1$–$C_{20}$alkyl, $C_2$–$C_6$alkenyl, $C_2$–$C_6$alkynyl, $C_3$–$C_8$cycloalkyl or aryl or $R_7$ and $R_8$ together form $C_4$–$C_6$alkylene, oxa-$C_3$–$C_5$alkylene or aza-$C_3$–$C_5$alkylene wherein the alkylene, oxaalkylene and azaalkylene groups are unsubstituted or substituted;

especially $R_1$ is —$SO_2$—$R_6$, $R_6$ is —N($R_7$)$R_8$ and $R_7$ and $R_8$ are each independently of the other hydrogen, $C_1$–$C_{20}$alkyl, $C_2$–$C_6$alkenyl, $C_2$–$C_6$alkynyl, halo-$C_1$–$C_{10}$alkyl, halo-$C_2$–$C_6$alkenyl, halo-$C_2$–$C_6$alkynyl, $C_3$–$C_8$cycloalkyl, halo-$C_3$–$C_8$cycloalkyl, $C_3$–$C_8$cycloalkyl-$C_1$14 $C_6$alkyl, $C_1$–$C_6$alkoxy-$C_1$–$C_{10}$alkyl, cyano-$C_1$–$C_6$alkyl, or an aryl, aryl-$C_1$-$C_6$alkyl or aryloxy-$C_1$-$C_6$alkyl group, wherein the aryl radical is unsubstituted or substituted by from one to three substituents, selected from the group consisting of halogen, $C_1$-$C_4$alkyl, nitro, cyano, $C_1$-$C_4$alkoxy, phenoxy, $C_1$-$C_6$alkylcarbonyloxy, halo-$C_1$-$C_4$alkyl and halo-$C_1$-$C_4$alkoxy, or $R_7$ and $R_8$ together form a straight-chained $C_4$-$C_6$-alkylene group, a straight-chained oxa-$C_3$-$C_5$alkylene group bonded via carbon, or a straight-chained aza-$C_3$-$C_5$alkylene group bonded via carbon, the alkylene, oxaalkylene or azaalkylene group being unsubstituted or mono- or di-substituted by methyl;

more especially $R_1$ is —$SO_2$—$R_6$, $R_6$ is —$N(R_7)R_8$ and $R_7$ and $R_8$ are each independently of the other hydrogen, unsubstituted $C_1$-$C_{20}$alkyl, $C_2$-$C_6$alkenyl, $C_2$-$C_6$alkynyl, $C_3$-$C_8$cycloalkyl or aryl, or substituted $C_1$-$C_{20}$alkyl, $C_2$-$C_6$alkenyl, $C_2$-$C_6$alkynyl, $C_3$-$C_8$cycloalkyl or aryl;

more especially $R_1$ is —$SO_2$—$R_6$, $R_6$ is —$N(R_7)R_8$ and $R_7$ and $R_8$ are each independently of the other hydrogen, $C_1$-$C_{20}$alkyl, $C_2$-$C_6$alkenyl, $C_2$-$C_6$alkynyl, halo-$C_1$-$C_{10}$alkyl, halo-$C_2$-$C_6$alkenyl, halo-$C_2$-$C_6$alkynyl, $C_3$-$C_8$cycloalkyl, halo-$C_3$-$C_8$cycloalkyl, $C_3$-$C_8$cycloalkyl-$C_1$-$C_6$alkyl, $C_1$-$C_6$alkoxy-$C_1$-$C_{10}$alkyl, cyano-$C_1$-$C_6$alkyl, or an aryl, aryl-$C_1$-$C_6$alkyl or aryloxy-$C_1$-$C_6$alkyl group, wherein the aryl radical is unsubstituted or substituted by from one to three substituents, selected from the group consisting of halogen, $C_1$-$C_4$alkyl, nitro, cyano, $C_1$-$C_4$alkoxy, phenoxy, $C_1$-$C_6$alkylcarbonyloxy, halo- $C_1$-$C_4$alkyl and halo-$C_1$-$C_4$alkoxy;

more especially $R_1$ is —$SO_2$—$R_6$, $R_6$ is —$N(R_7)R_8$ and $R_7$ and $R_8$ are each independently of the other hydrogen, $C_1$-$C_6$alkyl, $C_3$-$C_8$cycloalkyl, $C_3$-$C_8$cycloalkyl-$C_1$-$C_4$alkyl, $C_1$-$C_4$alkoxy-$C_1$-$C_4$alkyl, unsubstituted phenyl or phenyl which is unsubstituted or carries from one to three substituents, selected from the group consisting of halogen, $C_1$-$C_4$alkyl, nitro, $C_1$-$C_4$alkoxy, halo-$C_1$-$C_4$alkyl and halo-$C_1$-$C_4$alkoxy;

more especially $R_1$ is —$SO_2$—$R_6$, $R_6$ is —$N(R_7)R_8$ and $R_7$ and $R_8$ are each independently of the other hydrogen or $C_1$-$C_6$alkyl;

more especially $R_1$ is —$SO_2$—$R_6$, $R_6$ is —$N(R_7)R_8$, $R_7$ is hydrogen or $C_1$-$C_6$alkyl and $R_8$ is $C_1$-$C_4$alkyl.

(8) a compound of formula I, wherein
$R_1$ is —$SO_2$—$R_6$, $R_6$ is —$N(R_7)R_8$ and $R_7$ and $R_8$ together form $C_4$-$C_6$alkylene, oxa-$C_3$-$C_5$-alkylene or aza-$C_3$-$C_5$alkylene wherein the alkylene, oxaalkylene and azaalkylene groups are unsubstituted or substituted;

especially $R_1$ is —$SO_2$—$R_6$, $R_6$ is —$N(R_7)R_8$ and $R_7$ and $R_8$ together form a straight-chained $C_4$-$C_6$alkylene group, a straight-chained oxa-$C_3$-$C_5$alkylene group bonded via carbon, or a straight-chained aza-$C_3$-$C_5$alkylene group bonded via carbon, the alkylene, oxaalkylene or azaalkylene group being unsubstituted or mono- or di-substituted by methyl;

more especially $R_1$ is —$SO_2$—$R_6$, $R_6$ is —$N(R_7)R_8$ and $R_7$ and $R_8$ together form an unsubstituted straight-chained $C_4$-$C_6$alkylene group or an unsubstituted straight-chained oxa-$C_3$-$C_5$alkylene group bonded via carbon;

more especially $R_1$ is —$SO_2$—$R_6$, $R_6$ is —$N(R_7)R_8$ and $R_7$ and $R_8$ together form tetramethylene, pentamethylene or —$CH_2$—$CH_2$—O—$CH_2$—$CH_2$—.

(9) a compound of formula I, wherein
$R_1$ is $C_3$-$C_8$cycloalkyl, halo-$C_3$-$C_8$cycloalkyl, $C_3$-$C_8$cycloalkyl-$C_1$-$C_6$alkyl or halo-$C_3$-$C_8$-cycloalkyl-$C_1$-$C_6$alkyl;
especially $R_1$ is $C_3$-$C_8$cycloalkyl.

(10) a compound of formula I, wherein
$R_1$ is —CO—$R_9$ and $R_9$ is hydroxy, unsubstituted $C_1$-$C_{10}$alkyl, $C_2$-$C_6$alkenyl, $C_2$-$C_6$alkynyl, $C_3$-$C_8$cycloalkyl, aryl or aryloxy, or substituted $C_1$-$C_{10}$alkyl, $C_2$-$C_6$alkenyl, $C_2$-$C_6$alkynyl, $C_3$-$C_8$cycloalkyl, aryl or aryloxy, or is —$N(R_{10})R_{11}$ and $R_{10}$ and $R_{11}$ are each independently of the other hydrogen, unsubstituted $C_1$-$C_{20}$alkyl, $C_2$-$C_6$alkenyl, $C_2$-$C_6$alkynyl, $C_3$-$C_8$cycloalkyl, aryl, pyridyl or quinolinyl, or substituted $C_1$-$C_{20}$alkyl, $C_2$-$C_6$alkenyl, $C_2$-$C_6$alkynyl, $C_3$-$C_8$cycloalkyl, aryl, pyridyl or quinolinyl, or $R_{10}$ and $R_{11}$ together form $C_4$-$C_6$alkylene, oxa-$C_3$-$C_5$alkylene or aza-$C_3$-$C_5$alkylene wherein the alkylene, oxaalkylene and azaalkylene groups are unsubstituted or substituted;

especially $R_1$ is —CO—$R_9$ and $R_9$ is hydroxy, $C_1$-$C_{10}$alkyl, halo-$C_1$-$C_{10}$alkyl, $C_1$-$C_6$alkoxy-$C_1$-$C_6$alkyl, $C_2$-$C_6$alkenyl, $C_2$-$C_6$alkynyl, halo-$C_2$-$C_6$alkenyl, halo-$C_2$-$C_6$alkynyl, $C_3$-$C_8$cycloalkyl, $C_3$-$C_8$cycloalkyl-$C_1$-$C_6$alkyl, halo-$C_3$-$C_8$cycloalkyl, —$N(R_{10})R_{11}$ or an aryl, aryloxy, aryl-$C_1$-$C_6$alkyl or aryloxy-$C_1$-$C_4$alkyl group, wherein the aryl radical is unsubstituted or substituted by from one to three substituents, selected from the group consisting of halogen, $C_1$-$C_4$alkyl, halo-$C_1$-$C_4$alkyl, nitro, cyano and $C_1$-$C_4$alkoxy, and $R_{10}$ and $R_{11}$ are each independently of the other hydrogen, $C_1$-$C_{20}$alkyl, $C_2$-$C_6$alkenyl, $C_2$-$C_6$alkynyl, halo-$C_1$-$C_{10}$alkyl, halo-$C_2$-$C_6$alkenyl, halo-$C_2$-$C_6$alkynyl, $C_3$-$C_8$cycloalkyl, halo-$C_3$-$C_8$cycloalkyl, halo-$C_3$-$C_8$cycloalkyl-$C_1$-$C_6$alkyl, $C_3$-$C_8$cycloalkyl-$C_1$-$C_6$alkyl, $C_1$-$C_6$alkoxy-$C_1$-$C_6$alkyl, or an aryl, pyridyl, quinolinyl, aryl-$C_1$-$C_6$alkyl or pyridyl-$C_1$-$C_6$alkyl group, which is unsubstituted or ring-substituted by from one to three substituents, selected from the group consisting of halogen, $C_1$-$C_4$alkyl, halo-$C_1$-$C_4$alkyl, nitro, cyano, $C_1$-$C_4$alkoxy, halo-$C_1$-$C_4$alkoxy and phenoxy, or $R_{10}$ and $R_{11}$ together form a straight-chained $C_4$-$C_6$alkylene group, a straight-chained oxa-$C_3$-$C_5$alkylene group bonded via carbon, or a straight-chained aza-$C_3$-$C_5$alkylene group bonded via carbon, the alkylene, oxaalkylene or azaalkylene group being unsubstituted or mono- or di-substituted by methyl;

more especially $R_1$ is —CO—$R_9$ and $R_9$ is hydroxy, unsubstituted $C_1$-$C_{10}$alkyl, $C_2$-$C_6$alkenyl, $C_2$-$C_6$alkynyl, $C_3$-$C_8$cycloalkyl, aryl or aryloxy, or substituted $C_1$-$C_{10}$alkyl, $C_2$-$C_6$alkenyl, $C_2$-$C_6$alkynyl, $C_3$-$C_8$cycloalkyl, aryl or aryloxy;

more especially $R_1$ is —CO—$R_9$ and $R_9$ is hydroxy, $C_1$-$C_{10}$alkyl, halo-$C_1$-$C_{10}$alkyl, $C_1$-$C_6$-alkoxy-$C_1$-$C_6$alkyl, $C_2$-$C_6$alkenyl, $C_2$-$C_6$alkynyl, halo-$C_2$-$C_6$alkenyl, halo-$C_2C_6$alkynyl, $C_3$-$C_8$cycloalkyl, $C_3$-$C_8$cycloalkyl-$C_1$-$C_6$alkyl, halo-$C_3$-$C_8$cycloalkyl or an aryl, aryloxy, aryl-$C_1$-$C_6$alkyl or aryloxy-$C_1$-$C_4$alkyl group, wherein the aryl radical is unsubstituted or substituted by from one to three substituents, selected from the group consisting of halogen, $C_1$–$C_4$alkyl, halo-$C_1$–$C_4$alkyl, nitro, cyano and $C_1$–$C_4$alkoxy;

more especially $R_1$ is —CO—$R_9$ and $R_9$ is hydroxy, $C_1$–$C_{10}$alkyl, $C_3$–$C_8$cycloalkyl or an aryl or aryl-$C_1$–$C_4$alkyl group, wherein the aryl radical is unsubstituted or substituted by from one to three substituents, selected from the group consisting of halogen and nitro;

more especially $R_1$ is —CO—$R_9$ and $R_9$ is hydroxy, $C_1$–$C_{10}$alkyl, $C_3$–$C_8$cycloalkyl or a phenyl or phenyl-$C_1$–$C_4$alkyl group, wherein the phenyl radical is unsubstituted or substituted by 1 or 2 substituents, selected from the group consisting of halogen and nitro; more especially $R_1$ is —CO—$R_9$ and $R_9$ is hydroxy, $C_1$–$C_4$alkyl or unsubstituted phenyl-$C_1$–$C_4$alkyl.

(11) a compound of formula I, wherein
$R_1$ is —CO—$R_9$, $R_9$ is —N($R_{10}$)$R_{11}$ and $R_{10}$ and $R_{11}$ are each independently of the other hydrogen, unsubstituted $C_1$–$C_{20}$alkyl, $C_2$–$C_6$alkenyl, $C_2$–$C_6$alkynyl, $C_3$–$C_8$cycloalkyl, aryl, pyridyl or quinolinyl, or substituted $C_1$–$C_{20}$alkyl, $C_2$–$C_6$alkenyl, $C_2$–$C_6$alkynyl, $C_3$–$C_8$-cycloalkyl, aryl, pyridyl or quinolinyl, or $R_{10}$ and $R_{11}$ together form $C_4$–$C_6$alkylene, oxa-$C_3$–$C_5$alkylene or aza-$C_3$–$C_5$alkylene wherein the alkylene, oxaalkylene and azaalkylene groups are unsubstituted or substituted;

especially $R_1$ is —CO—$R_9$, $R_9$ is —N($R_{10}$)$R_{11}$ and $R_{10}$ and $R_{11}$ are each independently of the other hydrogen, $C_1$–$C_{20}$alkyl, $C_2$–$C_6$alkenyl, $C_2$–$C_6$alkynyl, halo-$C_1$–$C_{10}$alkyl, halo-$C_2$–$C_6$alkenyl, halo-$C_2$–$C_6$alkynyl, $C_3$–$C_8$cycloalkyl, halo-$C_3$–$C_8$cycloalkyl, halo-$C_3$–$C_8$cycloalkyl-$C_1$–$C_6$alkyl, $C_3$–$C_8$cycloalkyl-$C_1$–$C_6$alkyl, $C_1$–$C_6$alkoxy-$C_1$–$C_6$alkyl, or an aryl, pyridyl, quinolinyl, aryl-$C_1$–$C_6$alkyl or pyridyl-$C_1$–$C_6$alkyl group, which is unsubstituted or ring-substituted by from one to three substituents, selected from the group consisting of halogen, $C_1$–$C_4$alkyl, halo-$C_1$–$C_4$alkyl, nitro, cyano, $C_1$–$C_4$alkoxy, halo-$C_1$–$C_4$alkoxy and phenoxy, or $R_{10}$ and $R_{11}$ together form a straight-chained $C_4$–$C_6$alkylene group, a straight-chained oxa-$C_3$–$C_5$alkylene group bonded via carbon, or a straight-chained aza-$C_3$–$C_5$alkylene group bonded via carbon, the alkylene, oxaalkylene or azaalkylene group being unsubstituted or mono- or di-substituted by methyl;

more especially $R_1$ is —CO—$R_9$, $R_9$ is —N($R_{10}$)$R_{11}$ and $R_{10}$ and $R_{11}$ are each independently of the other hydrogen, unsubstituted $C_1$–$C_{20}$alkyl, $C_2$–$C_6$alkenyl, $C_2$–$C_6$alkynyl, $C_3$–$C_8$cycloalkyl, aryl, pyridyl or quinolinyl, or substituted $C_1$–$C_{20}$alkyl, $C_2$–$C_6$alkenyl, $C_2$–$C_6$alkynyl, $C_3$–$C_8$cycloalkyl, aryl, pyridyl or quinolinyl;

more especially $R_1$ is —CO—$R_9$, $R_9$ is —N($R_{10}$)$R_{11}$ and $R_{10}$ and $R_{11}$ are each independently of the other hydrogen, $C_1$–$C_{20}$alkyl, $C_2$–$C_6$alkenyl, $C_2$–$C_6$alkynyl, halo-$C_1$–$C_{10}$alkyl, halo-$C_2$–$C_6$alkenyl, halo-$C_2$–$C_6$alkynyl, $C_3$–$C_8$cycloalkyl, halo-$C_3$–$C_8$cycloalkyl, halo-$C_3$–$C_8$cycloalkyl-$C_1$–$C_6$alkyl, $C_3$–$C_8$cycloalkyl-$C_1$–$C_6$alkyl, $C_1$–$C_6$alkoxy-$C_1$–$C_6$alkyl, or an aryl, pyridyl, quinolinyl, aryl-$C_1$–$C_6$alkyl or pyridyl-$C_1$–$C_6$alkyl group, which is unsubstituted or ring-substituted by from one to three substituents, selected from the group consisting of halogen, $C_1$–$C_4$alkyl, halo-$C_1$–$C_4$alkyl, nitro, cyano, $C_1$–$C_4$alkoxy, halo-$C_1$–$C_4$alkoxy and phenoxy;

more especially $R_1$ is —CO—$R_9$, $R_9$ is —N($R_{10}$)$R_{11}$ and $R_{10}$ and $R_{11}$ are each independently of the other hydrogen, $C_1$–$C_{20}$alkyl, $C_3$–$C_8$cycloalkyl, $C_3$–$C_8$cycloalkyl-$C_1$–$C_4$alkyl, $C_1$–$C_4$alkoxy-$C_1$–$C_4$alkyl, or an aryl, pyridyl, quinolinyl, aryl-$C_1$–$C_6$alkyl or pyridyl-$C_1$–$C_6$alkyl group, which is unsubstituted or ring-substituted by from one to three substituents, selected from the group consisting of halogen, $C_1$–$C_4$alkyl, halo-$C_1$–$C_4$alkyl, nitro, cyano, $C_1$–$C_4$alkoxy, halo-$C_1$–$C_4$alkoxy and phenoxy;

more especially $R_1$ is —CO—$R_9$, $R_9$ is —N($R_{10}$)$R_{11}$ and $R_{10}$ and $R_{11}$ are each independently of the other hydrogen, $C_1$–$C_{10}$alkyl, $C_3$–$C_8$cycloalkyl, $C_3$–$C_8$cycloalkyl-$C_1$–$C_4$alkyl, $C_1$–$C_4$-alkoxy-$C_1$–$C_4$alkyl, or a phenyl, pyridyl, quinolinyl, phenyl-$C_1$–$C_4$alkyl or pyridyl-$C_1$–$C_4$alkyl group, which is unsubstituted or ring-substituted by from 1 or 2 substituents, selected from the group consisting of halogen, $C_1$–$C_4$alkyl, halo-$C_1$–$C_4$alkyl, nitro, cyano, $C_1$–$C_4$alkoxy, halo-$C_1$–$C_4$alkoxy and phenoxy.

(12) a compound of formula I, wherein
$R_1$ is —CO—$R_9$, $R_9$ is —N($R_{10}$)$R_{11}$ and $R_{10}$ and $R_{11}$ together form $C_4$–$C_6$alkylene, oxa-$C_3$–$C_5$-alkylene or aza-$C_3$–$C_5$alkylene wherein the alkylene, oxaalkylene and azaalkylene groups are unsubstituted or substituted;

especially $R_1$ is —CO—$R_9$, $R_9$ is —N($R_{10}$)$R_{11}$ and $R_{10}$ and $R_{11}$ together form a straight-chained $C_4$–$C_6$alkylene group, a straight-chained oxa-$C_3$–$C_5$alkylene group bonded via carbon, or a straight-chained aza-$C_3$–$C_5$alkylene group bonded via carbon, the alkylene, oxaalkylene or azaalkylene group being unsubstituted or mono- or di-substituted by methyl;

more especially $R_1$ is —CO—$R_9$, $R_9$ is —N($R_{10}$)$R_{11}$ and $R_{10}$ and $R_{11}$ together form tetramethylene, pentamethylene, hexamethylene, —$CH_2$—$CH_2$—O—$CH_2$—$CH_2$— or —$CH_2$—$CH_2$—N($CH_3$)—$CH_2$—$CH_2$—.

(13) a compound of formula I, wherein $R_1$ is bonded in the 4-position of the phenyl ring shown in formula I,

(14) a compound of formula I, wherein
n is 0, 1 or 2 and $R_2$ is halogen, $C_1$–$C_4$alkyl or $CF_3$, the substituents $R_2$ being identical or different, when n is 2;
especially n is 0 or 1 and $R_2$ is halogen or $CF_3$;
more especially n is 0 or 1 and $R_2$ is chlorine or $CF_3$;
more especially n is 0.

(15) a compound of formula I, wherein
m is 1,3,5,7,9 or 11;
especially m is 3, 7 or 9;
more especially m is 3 or 9;
more especially m is 3.

(16) a compound of formula I, wherein
X is fluorine or chlorine;
especially X is fluorine.

(17) a compound of formula I, wherein
Y is hydrogen, fluorine or methyl;
especially Y is hydrogen.

(18) a compound of formula I, wherein
$R_{12}$ is hydrogen or unsubstituted or substituted $C_1$–$C_{10}$-alkyl;

especially $R_{12}$ is hydrogen, $C_1-C_{10}$-alkyl or benzyl, which is unsubstituted or ring-substituted by from one to three substituents, selected from the group consisting of nitro, halogen, $CF_3$, CN and $C_1-C_4$-alkyl;

more especially $R_{12}$ is hydrogen $C_1-C_6$-alkyl;

more especially $R_{12}$ is hydrogen.

Within the scope of the invention special preference is given to the compounds I mentioned in Examples A1 to A6.

Within the scope of the invention preference is given specifically to (a) 6,6)-difluorohex-5-enoic acid N-(4-trimethylsilylphenyl)amide, (b) 12,12-difluorododec-11-enoic acid N-(4-trimethylsilylphenyl)amide, (c) 6,6-difluorohex-5-enoic acid N-(3-trimethylsilylphenyl)amide, (d) 12,12-difluorododec-11-enoic acid N-(3-trimethylsilylphenyl)amide, (e) 6,6-difluorohex-5-enoic acid N-(4-phenylthiophenyl)amide, (f) 6,6-difluorohex-5-enoic acid N-(4-naphth-2-ylthiophenyl)amide, (g) 6,6-difluorohex-5-enoic acid N- [3-chloro-4-(4-methylphenylthio)phenyl]amide, (h) 6,6-difluorohex-5-enoic acid N-[4-(4-chlorophenylthio)phenyl]amide, (i) 12,12-difluorododec-11-enoic acid N-(4-dimethylaminosulfonylphenyl)amide, (j) 12,12-difluorododec-11-enoic acid N-(4-ethylaminosulfonylphenyl)amide and (k) 12,12,-difluorododec-11-enoic acid N-(4-propylsulfonylphenyl)amide.

The invention relates further to a process for the preparation of the compounds of formula I, in free form or in salt form, characterised in that a) a compound of formula

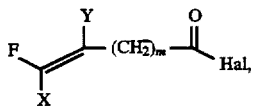

(II)

wherein X, Y and m are as defined for formula I and Hal is halogen, preferably chlorine or bromine, is reacted, optionally in an inert solvent and in the presence of an acid-binding agent, with a compound of formula

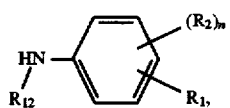

(III)

wherein $R_1$, $R_2$, $R_{12}$ and n are as defined for formula I, or a salt thereof or b) a compound of formula

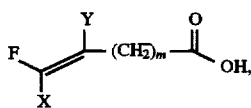

(IV)

wherein X, Y and m are as defined for formula I, is reacted, optionally in the presence of a condensation agent or a water-removing agent, with a compound of formula III or a salt thereof or c) a compound of formula

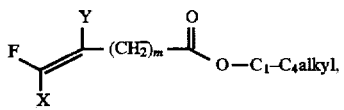

(V)

wherein X, Y and m are as defined for formula I, is reacted with a compound of formula III or a salt thereof and/or, if desired, a compound of formula I obtainable in accordance with the process or by a different method, in free form or in salt form, is converted into a different compound of formula I, a mixture of isomers obtainable in accordance with the process is separated and the desired isomer is isolated and/or a free compound of formula I obtainable in accordance with the process or by a different method is converted into a salt or a salt of a compound of formula I obtainable in accordance with the process or by a different method is converted into the free compound of formula I or into a different salt.

What has been said hereinabove for tautomers and/or salts of compounds I applies analogously to starting materials mentioned hereinabove and hereinafter with regard to the tautomers and/or salts thereof.

The reactions described hereinabove and hereinafter are carried out in a manner known per se, for example in the absence or, conventionally, in the presence of a suitable solvent or diluent or a mixture of these, the process being carried out, as required, with cooling, at room temperature or with heating, for example in a temperature range from approximately −80° C. to the boiling point of the reaction mixture, preferably from approximately −20° C. to approximately +150° C., and, if necessary, in a sealed container, under pressure, in an inert gas atmosphere and/or under anhydrous conditions. Particularly advantageous reaction conditions can be found in the Examples.

The reaction of process variant a) is preferably carried out in an inert, hydroxy-group-free solvent or diluent in the presence of an organic base, for example in the presence of pyridine, 4-dimethylaminopyridine, 4-pyrrolidinopyridine, lutidine, collidine, a trialkylamine, an N,N-dialkylaniline, or a bicyclic, non-nucleophilic base, such as 1,4-diazabicyclo [2.2.2]octane (DABCO), 1,5-diazabicyclo[4.3.0]non-5-ene (DBN) or 1,8-diazabicyclo[5.4.0]undec-7-ene (DBU). Suitable solvents or diluent3 are, for example, aliphatic and aromatic hydrocarbons, such as benzene, toluene, xylenes, petroleum ether, hexane; halogenated hydrocarbons, such as chlorobenzene, dichloromethane, ethylene chloride, chloroform, carbon tetrachloride, tetrachloroethylene; ethers and ethereal compounds, such as dialkyl ethers (diethyl ether, diisopropyl ether, tert-butyl methyl ether, etc.), anisole, dioxane, tetrahydrofuran; nitrites, such as acetonitrile, propionitrile; esters, such as ethyl acetate, propyl acetate or butyl acetate; ketones, such as acetone, diethyl ketone, methyl ethyl ketone; and mixtures of such solvents or diluents with one another. It is also possible, however, to carry out the reaction in an excess of one of the above-mentioned bases, or instead of a base it is also possible to use a second equivalent or a larger excess of the compound III. The reaction is generally carried out at temperatures of from −30° C. to +70° C., preferably from −10° C. to +50° C. The reaction is carried out at ambient pressure, although it could also be carried out at elevated or reduced pressure.

In process variant b) the reaction is advantageously carried out in the presence of a condensation agent, for example in the presence of phosphorous acid dichloride phenyl esters, benzenephosphonic acid dichloride, 2,4,6-trichloros-triazine, carbonic acid diimidazolide, a carbodiimide, such as N,N'-dicyclohexylcarbodiimide (DCC), aluminium oxide, titanium tetrachloride, 2,2,4,4,6,6-hexachloro-1,3,5-triazatriphosphorine or chloroformic acid lower alkyl esters, such as chloroformic acid isobutyl ester. The operation is preferably carried out in the presence of a base, for example in the presence of an organic amine, such as a trialkylamine (trimethylamine, triethylamine, triisopropylamine or diisopropylethylamine), a pyridine (pyridine itself, 4-dimethylaminopyridine or 4-pyrrolidinopyridine), a morpholine (N-methylmorpholine) or an N,N-dialkylaniline (N,N-dimethylaniline or N-methyl-N-ethylaniline). The reaction is advantageously carried out in the presence of an inert solvent or diluent at temperatures of from −30° C. to +70° C., preferably from −10° C. to +50° C. Suitable solvents or diluents are, for example, aliphatic and aromatic hydrocarbons, such as benzene, toluene, xylenes, petroleum ether, hexane; halogenated hydrocarbons, such as chlorobenzene, methylene chloride, ethylene chloride, chloroform, carbon tetrachloride, tetrachloroethylene; ethers, such as dialkyl ethers (diethyl ether, diisopropyl ether, tert-butyl methyl ether etc.), anisole, dioxane, tetrahydrofuran; nitriles, such as acetonitrile, propionitrile; esters, such as ethyl acetate, propyl acetate or butyl acetate; and mixtures of such solvents with one another.

In process variant c) the reactions are advantageously carried out in the presence of an inert solvent or diluent at temperatures of from 0° to +120° C., preferably from 50° C. to +100° C. Solvents that come into consideration are, for example, those mentioned under variant a).

The compounds II, III, IV and V are known or can be prepared in accordance with processes known per se or in accordance with processes to which the present invention also relates.

Compounds I obtainable in accordance with the process or by a different method cam be converted in a manner known per se into different compounds I by replacing one or more substituents of the starting compound I in customary manner by (a) different substituent(s) according to the invention. For example, in a compound I substituents $R_2$ can be introduced into the phenyl radical. Depending on the choice of reaction conditions and starting materials suitable for each purpose, it is possible to replace only one substituent by another substituent according to the invention in a reaction step or to replace several substituents by other substituents according to the invention in the same reaction step.

Salts of compounds I can be prepared in a manner known per se. For example, salts of compounds I with bases are obtained by treatment of the free compounds with a suitable base or a suitable ion exchange reagent.

Salts of compounds I can be converted into the free compounds I in customary manner, for example by treatment with a suitable acid or a suitable ion exchange reagent.

Salts of a compound I can be converted into different salts of a compound I in a manner known per se.

Depending upon the procedure and the reaction conditions, compounds I having salt-forming properties can be obtained in free form or in the form of salts.

The compounds I, in free form or in salt form, may be in the form of one of the possible isomers or in the form of a mixture thereof, for example according to the number of asymmetric carbon atoms occurring in the molecule and the absolute and relative configuration thereof and/or according to the configuration of non-aromatic double bonds occurring in the molecule, they may be in the form of pure isomers, such as antipodes and/or diastereoisomers, or in the form of mixtures of isomers, such as mixtures of enantiomers, for example racemates, mixtures of diastereoisomers or mixtures of racemates. In particular, compounds of formula I wherein X is chlorine may be in the form of a double bond isomer in the E or Z form. The invention relates both to the pure isomers and to all possible mixtures of isomers and this is to be understood hereinbefore and hereinafter, even if stereochemical details are not specifically mentioned in each case.

Mixtures of diastereoisomers, mixtures of racemates and mixtures of double bond isomers of compounds I, in free form or in salt form, obtainable in accordance with the process—depending upon the starting materials and procedures chosen—or by other means, can be separated into the pure diastereoisomers or racemates in known manner on the basis of the physicochemical differences between the constituents, for example by fractional crystallisation, distillation and/or chromatography.

Correspondingly obtainable mixtures of enantiomers, such as racemates, can be separated into the optical antipodes by known methods, for example by recrystallisation from an optically active solvent, by chromatography on chiral adsorbents, for example high-pressure liquid chromatography (HPLC) on acetyl cellulose, with the aid of suitable microorganisms, by cleavage with specific, immobilised enzymes, via the formation of inclusion compounds, for example using chiral crown ethers, in which case only one enantiomer is complexed, or by conversion into diastereoisomeric salts and separation of the resulting mixture of diastereoisomers, for example on the basis of their different solubilities by fractional crystallisation, into the diastereoisomers from which the desired enantiomer can be freed by the action of suitable agents.

Apart from by the separation of corresponding mixtures of isomers, it is possible according to the invention to obtain pure diastereoisomers or enantiomers also by generally known methods of diastereoselective or enantioselective synthesis, for example by carrying out the process according to the invention with starting materials having correspondingly suitable stereochemistry.

It is advantageous in each case to isolate or synthesise the biologically more active isomer, for example enantiomer or diastereoisomer, or mixture of isomers, for example mixture of enantiomers or mixture of diastereoisomers, insofar as the individual components have different biological activity.

The compounds I, in free form or in salt form, can also be obtained in the form of their hydrates and/or may include other solvents, for example solvents that may be used for the crystallisation of compounds in solid form.

The invention relates to all those forms of the process according to which a compound obtainable as starting material or intermediate at any stage of the process is used as starting material and all or some of the remaining steps are carried out, or a starting material is used in the form of a derivative or a salt and/or its racemates or antipodes or, especially, is formed under the reaction conditions.

In the process of the present invention there are preferably used those starting materials and intermediates, in each case in free form or in salt form, which result in the compounds of formula I described at the beginning as being especially valuable, or their salts.

The invention relates especially to the preparation processes described in Examples A1 to A6.

The invention relates also to d) a process for the preparation of a compound of formula

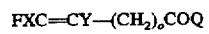

$FXC=CY—(CH_2)_nCOQ$         (IVa), wherein o is 3, 5, 7, 9 or 11, X is fluorine or chlorine, Q is —OH, halogen or —O—$C_1$-$C_4$alkyl and Y is hydrogen, fluorine or methyl, wherein a compound of formula

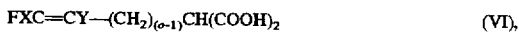
$FXC=CY-(CH_2)_{(o-1)}CH(COOH)_2$     (VI), wherein o is 3, 5, 7, 9 or 11, X is fluorine or chlorine and Y is hydrogen, fluorine or methyl, is decarboxylated, and, if desired, the resulting compound of formula IVa wherein Q is OH is converted with a halogenating agent into a compound of formula IVa wherein Q is a halogen atom, preferably chlorine, or with a compound of the formula $HOC_1$-$C_4$alkyl, preferably in the presence of an acid, into a compound of formula IVa wherein Q is —O—$C_1$-$C_4$alkyl, preferably —O—$CH_3$ or —O—$C_2H_5$, or for the preparation of a compound of formula IVa wherein Q is a group —$OC_1$-$C_4$alkyl, a compound of formula IVa wherein Q is halogen is reacted with a compound of the formula $HOC_1$-$C_4$alkyl.

The invention relates also to e) a process for the preparation of a compound of formula VI, wherein a compound of formula

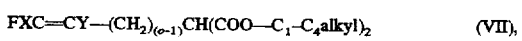
$FXC=CY-(CH_2)_{(o-1)}CH(COO-C_1-C_4alkyl)_2$     (VII), wherein o is 3, 5, 7, 9 or 11, X is fluorine or chlorine and Y is hydrogen, fluorine or methyl, is hydrolysed.

The invention relates also to f) a process for the preparation of a compound of formula VII, wherein HHal is removed from a compound of formula

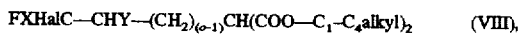
$FXHalC-CHY-(CH_2)_{(o-1)}CH(COO-C_1-C_4alkyl)_2$     (VIII), wherein o is 3, 5, 7, 9 or 11, X is fluorine or chlorine, Y is hydrogen, fluorine or methyl, and Hal is chlorine or bromine.

The invention relates also to g) a process for the preparation of a compound of formula VIII, wherein a compound of formula

$FXHalC-CHY-CHZ(CH_2)_{(o-2)}CH(COO-C_1-C_4alkyl)_2$     (IX), wherein o is 3, 5, 7, 9 or 11, X is fluorine or chlorine, Hal is chlorine or bromine, Y is hydrogen, fluorine or methyl and Z is bromine or iodine, is hydrogenated in the presence of a catalyst.

The invention relates also to h) a process for the preparation of a compound of formula IX, wherein a compound of formula

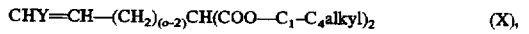
$CHY=CH-(CH_2)_{(o-2)}CH(COO-C_1-C_4alkyl)_2$     (X), wherein o is 3, 5, 7, 9 or 11 and Y is hydrogen, fluorine or methyl, is reacted with a compound of formula

CFXZHal     (XI), wherein X is fluorine or chlorine, Hal is chlorine or bromine and Z is bromine or iodine.

The reaction of process d) is carried out in a high-boiling solvent, for example in an amide, such as dimethylformamide, dimethylacetamide or N-methylpyrrolidone, in sulfolane or in dimethyl sulfoxide, but preferably in the absence of a solvent at from 80° to 180° C., preferably from 100° to 150° C.

The further reaction of process d) to form a compound IVa wherein Q is halogen is carried out with one of the customary halogenating agents, for example thionyl chloride, thionyl bromide, phosphorus oxychloride, phosphorus pentachloride or phosgene, in a solvent that is inert under the reaction conditions, as indicated under process variant a), or preferably in the absence of a solvent, optionally in the presence of a catalyst, for example an amide, for example dimethylformamide, at from 20° to 150° C., preferably from 80° to 120° C.

The further reaction of process d) to form a compound IVa wherein Q is —O—$C_1$-$C_4$alkyl is carried out in one of the solvents indicated under process variant a), but preferably in the absence of an inert solvent and in an excess of the alcohol to be used, in the presence of a catalytic amount of an acid, for example sulfuric acid or hydrochloric acid, at from 20° C. to the reflux temperature of the mixture, preferably at from 50° C. to 80° C.

Alternatively, a compound IVa wherein Q is —O—$C_1$-$C_4$alkyl can be obtained also by reaction of a compound IVa wherein Q is halogen with the corresponding alcohol. The operation is carried out in a solvent as indicated under variant a), but preferably in an excess of the alcohol to be used, in the presence of a hydroxy-group-free base, for (example a trialkylamine, dialkylaniline or a heterocyclic base, preferably pyridine, at from 0° C. to 80° C., preferably at room temperature.

The reaction of process e) may be carried out in one of the solvents mentioned under process variant b), but also in an alcohol, for example methanol, ethanol or isopropanol, in the presence of one of the bases mentioned under process variant b) or in the presence of an inorganic base, such as a carbonate, for example sodium carbonate or potassium carbonate, or a hydroxide, such as sodium hydroxide or potassium hydroxide, at a temperature of from 50° to 150° C., preferably at from 50° to 100° C.

In process variant f) the reaction preferably takes place in one of the solvents mentioned under process variant a) and in the presence of a reagent that removes hydrogen halide, for example a base, especially an inorganic base, such as sodium carbonate, potassium carbonate, sodium hydroxide or potassium hydroxide, or one of the organic bases mentioned under process variants a) and b) at a temperature of from 50° to 150° C., preferably at from 80° to 120° C.

The reaction of process g) is preferably carried out in one of the solvents mentioned under process variants a) and b) or in an alcohol, such as methanol or ethanol, and in the presence of one of the bases mentioned under process variant f), preferably an acetate, for example sodium acetate, and in the presence of a hydrogenation catalyst, for example Raney nickel or palladium, especially of catalysts applied to activated carbon, at normal pressure or at elevated pressure, preferably at normal pressure, at from 0° to 100° C., preferably from 10° to 30° C.

The reaction of process h) may be carried out in one of the solvents mentioned under process variant a) but preferably in the absence of a solvent, in the presence of a peroxide, preferably benzoyl peroxide, at normal pressure or at elevated pressure, preferably at normal pressure, at from −70° C. to +100° C.

The invention relates especially to the preparation processes described in Examples Z1 to Z7.

The present invention relates also to a compound of formula

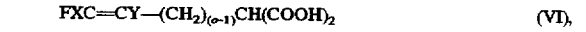
$FXC=CY-(CH_2)_{(o-1)}CH(COOH)_2$     (VI), wherein o is 3, 5, 7, 9 or 11, X is fluorine or chlorine and Y is hydrogen, fluorine or methyl.

The invention relates also to a compound of formula $$FXC=CY-(CH_2)_{(o-1)}CH(COO-C_1-C_4alkyl)_2 \quad (VII),$$

wherein o is 3, 5, 7, 9 or 11, X is fluorine or chlorine and Y is hydrogen, fluorine or methyl.

The invention relates also to a compound of formula $$FXHalC-CHY-(CH_2)_{(o-1)}CH(COO-C_1-C_4alkyl)_2 \quad (VIII),$$

wherein o is 3, 5, 7, 9 or 11, X is fluorine or chlorine, Y is hydrogen, fluorine or methyl and Hal is chlorine or bromine.

The invention relates also to a compound of formula $$FXHalC-CHY-CHZ(CH_2)_{(o-2)}CH(COO-C_1-C_4alkyl)_2 \quad (IX),$$

wherein o is 3, 5, 7, 9 or 11, X is fluorine or chlorine, Y is hydrogen, fluorine or methyl, Z is bromine or iodine and Hal is chlorine or bromine.

Of the compounds of formulae VI, VII, VIII and IX, preference is given to those wherein o is 3 or 9, X is fluorine, Y is hydrogen, Z is bromine and Hal is chlorine.

The compounds X and XI are known or can be prepared in accordance with methods known per se.

In the area of pest control, the compounds of formula I according to the invention are valuable preventive and/or curative active ingredients having a very advantageous biocidal spectrum even at low rates of concentration, while being well tolerated by warm-blooded animals, fish and plants. The compounds of the invention are effective against all or individual development stages of normally sensitive animal pests, but also of resistant animal pests, such as insects and representatives of the order Acarina. The insecticidal or acaricidal action or the compounds of the invention may manifest itself directly, i.e. in the mortality of the pests, which occurs immediately or only after some time, for example during moulting, or indirectly, for example in reduced oviposition and/or hatching rate, good activity corresponding to a mortality of at least 50 to 60%.

The mentioned animal pests include, for example:
of the order Lepidoptera, for example, Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;
of the order Coleoptera, for example, Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp., and Trogoderma spp.;
of the order Orthoptera, for example, Blatta spp., Blattella spp., Gryllotalpa spp., *Leucophaea maderae*, Locusta spp., Periplaneta spp. and Schistocerca spp.;
of the order Isoptera, for example, Reticulitermes spp.;
of the order Psocoptera, for example, Liposcelis spp.;
of the order Anoplura, for example, Haematopinus spp., Linognathus spp., Pediculus spp., Pemphigus spp. and Phylloxera spp.;
of the order Mallophaga, for example, Damalinea spp. and Trichodectes spp.;
of the order Thysanoptera, for example, Frankliniella spp., Hercinothrips spp., Taeniothrips spp., *Thrips palmi, Thrips tabaci* and *Scirtothrips aurantii*;
of the order Heteroptera, for example, Cimex spp., *Distantiella theobroma*, Dysdercus spp., Euchistus spp., Eurygaster spp., Leptocorisa spp., Nezara spp., Piesma spp., Rhodnius spp., *Sahlbergella singularis*, Scotinophara spp. and Triatoma spp.;
of the order Homoptera, for example,

*Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma larigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum, Trioza eryutreae* and *Unaspis citri*;
of the order Hymenoptera, for example, Acromyrmex, Atta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;
of the order Diptera, for example, Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami*, Phorbia spp., *Rhagoletis pomonella*, Sciara spp., Stomoxys spp., Tabanus spp., Tannia spp. and Tipula spp.;
of the order Siphonaptera, for example, Ceratophyllus spp. and *Xenopsylla cheopis*;
of the order Thysanura, for example,

*Lepisma saccharina*; and
of the order Acarina, for example,

*Acarus siro, Aceria sheldoni, Aculus schlechtendali*, Amblyomma spp., Argas spp., Boophilus spp., Brevipalpus spp., *Bryobia praetiosa*, Calipitrimerus spp., Chorioptes spp., *Dermanyssus gallinae, Eotetranychus carpini*, Eriophyes spp., Hyalomma spp., Ixodes spp., *Olygonychus pratensis*, Ornithodoros spp., Panonychus spp., *Phyllocoptruta oleivora, Polyphagotarsonemus latus*, Psoroptes spp., Rhipicephalus spp., Rhizoglyphus spp., Sarcopte s spp., Tarsonemus spp. and Tetranychus spp.

With the compounds according to the invention it is possible to control, i.e. to inhibit or destroy, pests of the mentioned type occurring especially on plants, more especially on useful plants and ornamentals in agriculture, in horticulture and in forestry, or on parts of such plants, such as the fruit, blossom, leaves, stems, tubers or roots, while some of the parts of the plants that grow later are also protected against those pests.

Target crops are especially cereals, such as wheat, barley, rye, oats, rice, maize and sorghum; beet, such as sugar beet and fodder beet; fruit, such as pomes, stone fruit and soft fruit, such as apples, pears, plums, peaches, almonds, cherries, or berries, for example strawberries, raspberries or blackberries; leguminous plants, such as beans, lentils, peas and soybeans; oil plants, such as rape, mustard, poppy, olives, sunflowers, coconut, castor oil plants, cocoa beans and groundnuts; cucumber plants, such as marrows, cucumber and melons; fibre plants, such as cotton, flax, hemp and jute; citrus fruit, such as oranges, lemons, grapefruit and mandarins; vegetables, such as spinach, lettuce, asparagus, cabbages, carrots, onions, tomatoes, potatoes and paprika; lauraceae, such as avocados, cinnamon and camphor; and tobacco, nuts, coffee, aubergines, sugar cane, tea, pepper, vines, hops, bananas and natural rubber plants, as well as ornamentals.

The compounds of the invention are suitable especially for controlling *Boophilus microplus, Nilaparvata lugens* and *Tetranychus urticae*, especially for controlling pests in crops of vegetables, fruit and rice.

Further areas of use of the compounds according to the invention are the protection of stored goods and stocks and materials, and also in the hygiene sector, especially the protection of domestic animals and productive livestock against pests of the mentioned type.

The invention therefore relates also to pesticidal compositions, such as emulsifiable concentrates, suspension concentrates, directly sprayable or dilutable solutions, coatable pastes, dilute emulsions, wettable powders, soluble powders, dispersible powders, wettable powders, dusts, granules or encapsulations in polymer substances, comprising—at least—one of the compounds of the invention, the type of formulation being chosen in accordance with the intended objectives and prevailing circumstances.

The active ingredient is used in those compositions in pure form: a solid active ingredient is used, for example, in a specific particle size, or preferably together with—at least—one of the adjuvants customary in formulation technology, such as extenders, for example solvents or solid carriers, or surface-active compounds (surfactants).

Suitable solvents are, for example: optionally partially hydrogenated aromatic hydrocarbons, preferably the fractions of alkylbenzenes containing 8 to 12 carbon atoms, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and their ethers and esters, such as propylene glycol, dipropylene glycol ether, ethylene glycol or ethylene glycol monomethyl or monoethyl ether, ketones, such as cyclohexanone, isophorone or diacetone alcohol, strongly polar solvents, such as N-methylpyrrolid-2-one, dimethyl sulfoxide or N,N-dimethylformamide, water, vegetable oils or epoxidised vegetable oils, such as rape oil, castor oil, coconut oil or soybean oil or epoxidised rape oil, castor oil, coconut oil or soybean oil, and silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, such as pumice, broken brick, sepiolite or bentonite; and suitable nonsorbent carriers are calcite or sand. In addition, a great number of granulated materials of inorganic or organic nature can be used, especially dolomite or pulverised plant residues.

Depending on the nature of the compound to be formulated, suitable surface-active compounds are non-ionic, cationic and/or anionic surfactants or mixtures of surfactants having go emulsifying, dispersing and wetting properties. The surfactants listed below are to be regarded merely as examples; many more surfactants customarily employed in formulation technology and suitable for use according to the invention are described in the relevant literature.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates. Examples are stearyltrimethylammonium chloride and benzyl-di(2-chloroethyl)ethylammonium bromide.

Both water-soluble soaps and water-soluble synthetic surface-active compounds are suitable anionic surfactants. Suitable soaps are the alkali metal salts, alkaline earth metal salts and unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tall oil; mention may also be made of fatty acid methyltaurin salts. More frequently, however, synthetic surfactants are used, especially fatty sulfonates, fatty sulfates, sulfonated benzimidazole derivatives or alkylarylsulfonates. The fatty sulfonates or sulfates are usually in the form of alkali metal salts, alkaline earth metal salts or unsubstituted or substituted ammonium salts and generally contain a $C_8$–$C_{22}$alkyl radical, which also includes the alkyl moiety of acyl radicals; there may be mentioned by way of example the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing approximately 8 to 22 carbon atoms. Examples of alkylarylsulfonates are the sodium, calcium or triethanolammonium salts of dodecylbenzenesulfonic acid, dibutylnaphthalenesulfonic acid or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide, or phospholipids.

The compositions usually comprise 0.1 to 99%, preferably 0.1 to 95%, of active ingredient, and 1 to 99.9%, preferably 5 to 99.9%, of—at least—one solid or liquid adjuvant, it generally being possible for 0 to 25%, preferably 0.1 to 20%, of the composition to be surfactants (in each case percentages are by weight). Whereas commercial products will preferably be formulated as concentrates, the end user will normally employ dilute formulations which have considerably lower active ingredient concentrations.

Preferred formulations have especially the following composition (throughout, percentages are by weight):

| Emulsifiable concentrates: | |
| --- | --- |
| active ingredient: | 1 to 95%, preferably 5 to 20% |
| surfactant: | 1 to 30%, preferably 10 to 20% |
| solvent: | 5 to 98%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 99%, preferably 15 to 98% |
| Granules: | |
| active ingredient: | 0.5 to 30%, preferably 3 to 15% |
| solid carrier: | 99.5 to 70%, preferably 97 to 85% |

The activity of the compositions according to the invention can be substantially broadened and adapted to prevailing circumstances by the addition of other insecticidal active ingredients. Examples of suitable additional active ingredients include representatives of the following classes of compounds: organophosphorus compounds, nitrophenols and derivatives, formamidines, acylureas, carbamates, pyrethroids, nitroenamines and derivatives, pyrroles, thioureas and derivatives, chlorinated hydrocarbons, and Bacillus thuringiensis preparations. The compositions according to the invention may also comprise further solid or liquid adjuvants, such as stabilisers, for example vegetable oils or epoxidised vegetable oils (e.g. epoxidised coconut oil, rape oil or soybean oil), antifoams, for example silicone oil, preservatives, viscosity regulators, binders and/or tackifiers, as well as fertilisers or other active ingredients for obtaining special effects, for example acaricides, bactericides, fungicides, nematicides, molluscicides or selective herbicides.

The compositions according to the invention are prepared in known manner, in the absence of adjuvants, for example by grinding, sieving and/or compressing a solid active ingredient or mixture of active ingredients, for example to a specific particle size, and in the presence of at least one adjuvant, for example by intimately mixing and/or grinding the active ingredient or mixture of active ingredients with the adjuvant(s). The invention relates also to those processes for the preparation of the compositions according to the invention and to the use of the compounds I in the preparation of those compositions.

The invention relates also to the methods of application of the compositions, i.e. the methods of controlling pests of the mentioned type, such as spraying, atomising, dusting, coating, dressing, scattering or pouring, which are selected in accordance with the intended objectives and prevailing circumstances, and to the use of the compositions for controlling pests of the mentioned type. Typical rates of concentration are, from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha.

A preferred method of application in the area of plant protection is application to the foliage of the plants (foliar application), the number of applications and the rate of application depending on the risk of infestation by the pest in question. However, the active ingredient can also penetrate the plants through the roots (systemic action) if the locus of the plants is impregnated with a liquid formulation or if the active ingredient is incorporated in solid form into the locus of the plants, for example into the soil, e.g. in granular form (soil application). In paddy rice crops, such granules may be applied in metered amounts to the flooded rice field.

The compositions according to the invention are also suitable for protecting plant propagation material, e.g. seed, such as fruit, tubers or grains, or plant cuttings, from animal pests. The propagation material can be treated with the formulation before planting: seed, for example, can be dressed before being sown. The compounds of the invention can also be applied to grains (coating), either by impregnating the grains with a liquid formulation or by coating them with a solid formulation. The formulation can also be applied to the planting site when the propagation material is being planted, for example to the seed furrow during sowing. The invention relates also to those methods of treating plant propagation material and to the plant propagation material thus treated.

The following Examples are intended to illustrate the invention. They do not limit the invention. Temperatures are given in degrees Celsius, mixture ratios of solvents in parts by volume.

PREPARATION EXAMPLES

Example Z1

6,6-Difluorohex-5-enoic acid

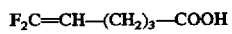

20.0 g of 2-(4,4-Difluorobut-3-en-1-yl)malonic acid are stirred under nitrogen for 30 hours at 130°. After cooling, the title compound is obtained in the form of a brown oil.

In an analogous manner it is also possible to obtain the other compounds of formula IVa, wherein Q is —OH.

Example Z2

6,6-Difluorohex-5-enoic acid chloride 6.5 ml of thionyl chloride are added dropwise, at room temperature, with stirring, to 7.5 g of 6,6-difluorohex-5-enoic acid and a drop of dimethylformamide. The mixture is then stirred at reflux temperature for 5 hours, the excess thionyl chloride is evaporated off in a rotary evaporator and the residue is distilled at 86° and 100 mbar. The title product is obtained in the form of a colourless fluid.

27

In an analogous manner it is also possible to obtain the other compounds of formula IVa, wherein Q is halogen.

Example Z3

6,6-difluorohex-5-enoic acid methyl ester 42.1 g of 6,6-difluorohex-5-enoic acid chloride are added slowly at 10° to 17.6 g of pyridine in 200 ml of methanol. The mixture is then stirred at room temperature for 5 hours. The excess methanol is evaporated off in a rotary evaporator and the residue is taken up in tert-butyl methyl ether and washed with water. The organic phase is dried over sodium sulfate and concentrated to dryness by evaporation. The residue is distilled at 60 mbar. The title compound is obtained in the form of a colourless oil.

In an analogous manner it is also possible to obtain the other compounds of formula IVa, wherein Q is —O—$C_1$-$C_4$alkyl.

Example Z4

2-(4,4-Difluorobut-3-en-1-yl)malonic acid

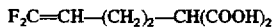

$F_2C=CH—(CH_2)_2—CH(COOH)_2$ 34.9 g of 2-(4,4-difluorobut-3-en-1-yl)malonic acid diethyl ester are added to 50 ml of methanol. 50 g of potassium carbonate dissolved in 150 ml of water are slowly added dropwise at room temperature and then the mixture is heated to reflux temperature and stirred at that temperature for 15 hours. The reaction mixture is concentrated to dryness by evaporation in a rotary evaporator and the residue is treated with concentrated hydrochloric acid until a pH value of 1 has been obtained and then extracted three times using 150 ml of diethyl ether each time. The combined ether phases are dried over sodium sulfate and concentrated by evaporation. The title compound is obtained in the form of a colourless oil.

In an analogous manner it is also possible to obtain the other compounds of formula VI.

Example Z5

2-(4,4-Difluorobut-3-en-1-yl)malonic acid diethyl ester

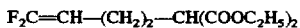

$F_2C=CH—(CH_2)_2—CH(COOC_2H_5)_2$ 150 g of 2-(4-chloro-4,4-difluoro-but-1-yl)malonic acid diethyl ester, 160 g of 1,8-diazabicyclo[5.4.0]undec-7-ene (DBU) and 250 ml of toluene are stirred for 15 hours at reflux temperature. After cooling, 200 ml of toluene are added and the reaction mixture is washed with 500 ml of water and then with 500 ml of 2N NaCl solution, dried over sodium sulfate and the solvent is evaporated off. The residue is distilled at 65° and 0.052 mbar. The title product is obtained in the form of a colourless oil.

In an analogous manner it is also possible to obtain the other compounds of formula VII.

28

Example Z6

2-(4—Chloro-4,4-difluoro-but-1-yl)malonic acid diethyl ester

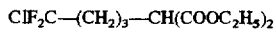

$ClF_2C—(CH_2)_3—CH(COOC_2H_5)_2$ 65.9 g of 2-(2-bromo-4-chloro-4,4-difluoro-but-1-yl) malonic acid diethyl ester, 600 ml of ethanol, 14.8 g of sodium acetate and 6.6 g of 5% palladium on activated carbon are treated with hydrogen at from 20° to 25° and under normal pressure until the absorption of hydrogen can no longer be detected. The reaction mixture is filtered over silica gel and then concentrated to dryness by evaporation in a rotary evaporator. The residue is taken up in 500 ml of n-hexane, the solution is filtered and the hexane phase is again concentrated to dryness by evaporation. The title compound is obtained in the form of a colourless oil.

In an analogous manner it is also possible to obtain the other compounds of formula VIII.

Example Z7

2-(2-Bromo-4-chloro-4,4-difluoro-but-1-yl)malonic acid diethyl ester

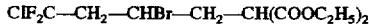

$ClF_2C—CH_2—CHBr—CH_2—CH(COOC_2H_5)_2$ 267 g of 2-allylmalonic acid diethyl ester and 25 g of benzoyl peroxide are placed in an autoclave, cooled to −50° and evacuated and then 500 g of bromochlorodifluoromethane are introduced. The reaction mixture is stirred at 65° for 60 hours. 300 ml of ethyl acetate are added and the reaction mixture is washed three times using 100 ml of saturated sodium hydrogen carbonate solution each time and twice using 100 ml of 2N sodium chloride solution each time. The organic phase is then dried over sodium sulfate, filtered over silica gel and concentrated to dryness by evaporation in a rotary evaporator. The residue is distilled at from 107° to 108° at 0.026 mbar. The title compound is obtained in the form of a yellow oil.

In an analogous manner it is also possible to obtain the other compounds of formula IX.

Example A1

6,6-Difluorohex-5-enoic acid N-(4-trimethylsilylphenyl)amide

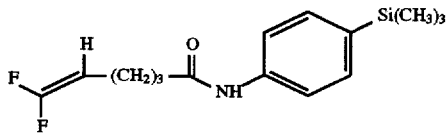

With cooling at 10°, 1.0 g of 6,6-difluorohex-5-enoic acid chloride is added to 1.0 g of 4-trimethylsilylaniline, 0.73 g of trithylamine and 10 mg of 4-N-pyrrolidinopyridine in 25 ml of tetrahydrofuran. The mixture is stirred for 2 hours at room temperature and then concentrated by evaporation in vacuo. The residue is taken up in toluene, the toluene phase is washed with water, dried over sodium sulfate and concentrated to dryness by evaporation. The residue is taken up in hexane:ethyl acetate (9:1) and filtered over silica gel. Evaporation of the filtrate yields the title compound having a melting point of 50°–51° (compound no. 1-1).

Example A2

6,6-Difluorohex-5-enoic acid N-(4-phenylthiophenyl)amide

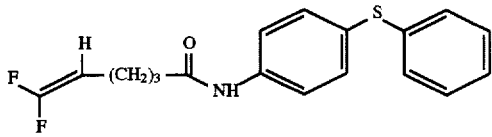

With cooling at 10°, 8.5 g of 6,6-difluorohex-5-enoic acid chloride are added to 10.0 g of 4-phenylthioaniline, 6.5 g of triethylamine and 100 mg of 4-N-pyrrolidinopyridine in 250 ml of tetrahydrofuran. The mixture is stirred for 2 hours at room temperature and then concentrated by evaporation in vacuo. The residue is taken up in toluene, the toluene phase is washed with water, dried over sodium sulfate and 90–95% of the amount of toluene is evaporated off in vacuo. While the mixture is still warm, a small amount of hexane is added, which causes the product to crystallise out. The mixture is cooled and filtered, and the filter residue is washed with hexane, yielding the title compound having a melting point of 80°–81° (compound no. 2-1).

Example A3

12,12-Difluorododec-11-enoic acid N-(4-propylsulfonylphenyl)amide

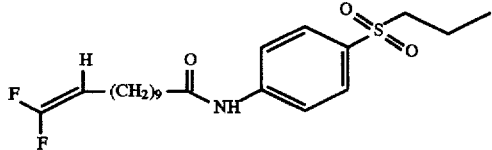

8.5 g of 12,12-difluorododec-11-enoic acid chloride are added at room temperature to 3.45 g of 4-propylsulfonylaniline, 2.5 g of triethylamine and 100 mg of 4-dimethylaminopyridine in 50 ml of toluene and the mixture is stirred for 2 days at room temperature. A further 50 ml of toluene is then added, the toluene phase is washed with water, dried over sodium sulfate and concentrated to dryness by evaporation in vacuo. The residue is chromatographed on silica gel with hexane:ethyl acetate (7:3), yielding the title compound having a melting point of 67°–70° C. (compound no. 3-4).

Example A4

6,6-Difluorohex-5-enoic acid N-(4-phenylthiophenyl)amide

At from 0° to 10°, 20.6 g of N,N'-dicyclohexylcarbodiimide are added, while stirring, in portions to 15 g of 6,6-difluorohex-5-enoic acid in 150 ml of dichloromethane. The mixture is stirred for a further 15 minutes under cooling and then 20.1 g of 4-phenylthioaniline are added in portions. The reaction mixture is stirred for 3 hours at room temperature and then filtered. The organic phase is washed with saturated sodium hydrogen carbonate solution and then dried over sodium sulfate. After concentration by evaporation, the residue is recrystallised from toluene/hexane, yielding the title compound having a melting point of from 80° to 81° (compound no. 2-1).

Example A5

12,12-Difluorododec-11-enoic acid N-(4-trimethylsilylphenyl)amide 2.5 g of 12,12-difluorododec-11-enoic acid methyl ester are added at room temperature to 1.53 g of 4-trimethylsilylaniline in 25 ml of toluene. The mixture is stirred for 2 hours at 80° and then concentrated by evaporation in vacuo. The residue is taken up in toluene, the toluene phase is washed with water, dried over sodium sulfate and concentrated to dryness by evaporation. The residue is taken up in hexane:ethyl acetate (9:1) and filtered over silica gel. Evaporation of the filtrate yields the title compound ($n_D^{24}$=1.5038; compound no. 1-2).

Example A6

In a manner analogous to that described in Examples A1 to A5 it is also possible to prepare the other compounds listed in Tables 1 to 4. In the "Phys. Data" column in these Tables, the temperatures given indicate the melting point of the compound in question, and "$n_D^T$" is the refractive index of the compound in question at the temperature T° C.

TABLE 1

| Comp. No. | $R_1$ | $(R_2)_n$ | S | Y | m | Phys. Data |
|---|---|---|---|---|---|---|
| 1-1 | 4-Si(CH$_3$)$_3$ | (n = 0) | F | H | 3 | 50–51° |
| 1-2 | 4-Si(CH$_3$)$_3$ | (n = 0) | F | H | 9 | $n_D^{24}$ = 1.5038 |
| 1-3 | 3-Si(CH$_3$)$_3$ | (n = 0) | F | H | 3 | $n_D^{23}$ = 1.5083 |
| 1-4 | 3-Si(CH$_3$)$_3$ | (n = 0) | F | H | 9 | $n_D^{22}$ = 1.4982 |
| 1-5 | 4-Si(CH$_3$)$_3$ | (n = 0) | F | H | 1 | |
| 1-6 | 4-Si(CH$_3$)$_3$ | (n = 0) | F | H | 5 | |
| 1-7 | 4-Si(CH$_3$)$_3$ | (n = 0) | F | H | 7 | |
| 1-8 | 3-Si(CH$_3$)$_3$ | (n = 0) | F | H | 5 | |
| 1-9 | 3-Si(CH$_3$)$_3$ | (n = 0) | F | H | 7 | |
| 1-10 | 2-Si(CH$_3$)$_3$ | (n = 0) | F | H | 3 | 50–51° |
| 1-11 | 2-Si(CH$_3$)$_3$ | (n = 0) | F | H | 5 | |
| 1-12 | 2-Si(CH$_3$)$_3$ | (n = 0) | F | H | 7 | |
| 1-13 | 2-Si(CH$_3$)$_3$ | (n = 0) | F | H | 9 | |
| 1-14 | 2-Si(CH$_3$)$_3$ | (n = 0) | F | H | 11 | |
| 1-15 | 2-Si(CH$_3$)$_3$ | 4-Cl | F | H | 9 | |
| 1-16 | 4-Si(CH$_3$)$_3$ | 2-Cl | F | H | 7 | |
| 1-17 | 4-Si(CH$_3$)$_3$ | 2-Cl | F | H | 9 | |
| 1-18 | 4-Si(CH$_3$)$_3$ | 2-Cl | F | H | 3 | |
| 1-19 | 3-Si(CH$_3$)$_3$ | 5-Cl | F | H | 3 | |
| 1-20 | 3-Si(CH$_3$)$_3$ | 5-Cl | F | H | 9 | |
| 1-21 | 4-Si(CH$_3$)$_3$ | (n = 0) | F | H | 11 | |
| 1-22 | 4-Si(CH$_3$)$_3$ | (n = 0) | F | CH$_3$ | 3 | |
| 1-23 | 4-Si(CH$_3$)$_3$ | (n = 0) | F | CH$_3$ | 5 | |
| 1-24 | 4-Si(CH$_3$)$_3$ | (n = 0) | F | CH$_3$ | 7 | |
| 1-25 | 4-Si(CH$_3$)$_3$ | (n = 0) | F | CH$_3$ | 9 | |
| 1-26 | 4-Si(CH$_3$)$_3$ | (n = 0) | F | F | 3 | |
| 1-27 | 4-Si(CH$_3$)$_3$ | (n = 0) | Cl | H | 3 | |
| 1-28 | 4-Si(CH$_3$)$_3$ | (n = 0) | Cl | H | 9 | |
| 1-29 | 4-Si(OCH$_3$)$_2$CH$_3$ | (n = 0) | F | H | 3 | |
| 1-30 | 2-Si(OCH$_3$)$_2$CH$_3$ | (n = 0) | F | H | 3 | |
| 1-31 | 4-Si(OC$_2$H$_5$)$_2$CH$_3$ | (n = 0) | F | H | 3 | |
| 1-32 | 2-Si(OC$_2$H$_5$)$_2$CH$_3$ | (n = 0) | F | H | 3 | |
| 1-33 | 4-Si(O-n-C$_3$H$_7$)$_2$CH$_3$ | (n = 0) | F | H | 3 | |
| 1-34 | 2-Si(O-n-C$_3$H$_7$)$_2$CH$_3$ | (n = 0) | F | H | 3 | |
| 1-35 | 4-Si(O$_2$H$_5$)$_2$CH$_3$ | (n = 0) | F | H | 9 | |

TABLE 2

Structure: F₂C=CH-(CH₂)ₘ-C(=O)-N(R₁₂)-C₆H₃(R₂)ₙ-S-R₄

| Comp. No. | R₄ | (R₂)ₙ | R₁₂ | m | Phys. Data |
|---|---|---|---|---|---|
| 2-1 | C₆H₅ | (n=0) | H | 3 | 80–81° |
| 2-2 | Naphth-2-yl | (n=0) | H | 3 | 111–112° |
| 2-3 | C₆H₄-4-CH₃ | 3-Cl | H | 3 | 68–69° |
| 2-4 | C₆H₄-4-Cl | (n=0) | H | 3 | 104–105° |
| 2-5 | Naphth-2-yl | 3-Cl | H | 3 | 86–87° |
| 2-6 | C₆H₄-4-Br | (n=0) | H | 3 | 113–115° |
| 2-7 | C₆H₅ | (n=0) | H | 9 | 77–79° |
| 2-8 | C₆H₅ | 3-Cl | H | 5 | |
| 2-9 | C₆H₅ | 3-Cl | H | 7 | |
| 2-10 | C₆H₄-2-Br | (n=0) | H | 3 | |
| 2-11 | C₆H₃-2,5-(Cl)₂ | (n=0) | H | 3 | |
| 2-12 | C₆H₄-2-Cl | (n=0) | H | 3 | |
| 2-13 | C₆H₄-2-C₂H₅ | (n=0) | H | 3 | |
| 2-14 | C₆H₄-4-t-C₄H₉ | (n=0) | H | 3 | |
| 2-15 | C₆H₄-4-i-C₃H₇ | (n=0) | H | 3 | |
| 2-16 | C₆H₄-4-c-C₆H₁₁ | (n=0) | H | 3 | |
| 2-17 | C₆H₄-4-OCH₃ | (n=0) | H | 3 | |
| 2-18 | C₆H₃-2,4-(CH₃)₂ | (n=0) | H | 3 | |
| 2-19 | C₆H₅ | (n=0) | H | 1 | |
| 2-20 | C₆H₅ | (n=0) | H | 5 | |
| 2-21 | C₆H₅ | (n=0) | H | 7 | |
| 2-22 | C₆H₄-4-Cl | (n=0) | H | 9 | |
| 2-23 | C₆H₅ | (n=0) | H | 11 | |
| 2-24 | C₆H₄-4-CH₃ | (n=0) | H | 9 | |
| 2-25 | Naphth-2-yl | (n=0) | H | 9 | |
| 2-26 | C₆H₃-3,4-(Cl)₂ | (n=0) | H | 3 | |
| 2-27 | Pyrid-2-yl | (n=0) | H | 3 | |
| 2-28 | Pyrimid-2-yl | (n=0) | H | 3 | |
| 2-29 | 5-NO₂-Pyrid-2-yl | (n=0) | H | 3 | |
| 2-30 | 5-CF₃-Pyrimid-2-yl | (n=0) | H | 3 | |
| 2-31 | 5-Cl-Pyrid-2-yl | (n=0) | H | 3 | |
| 2-32 | 5-CF₃-Pyrid-2-yl | (n=0) | H | 3 | |
| 2-33 | C₆H₄-4-CH₃ | 3-Cl | H | 9 | |
| 2-34 | C₆H₄-4-Cl | 3-Cl | H | 3 | |
| 2-35 | Pyrid-2-yl | 3-Cl | H | 3 | |
| 2-36 | Pyrimid-2-yl | 3-Cl | H | 3 | |
| 2-37 | Pyrid-2-yl | (n=0) | H | 9 | |
| 2-38 | Pyrid-2-yl | 3-Cl | H | 9 | |
| 2-39 | C₆H₃-3,4-(CH₃)₂ | (n=0) | H | 3 | |
| 2-40 | C₆H₅ | 3-CF₃ | H | 3 | $n_D^{24}$ = 1.5575 |
| 2-41 | C₆H₅ | (n=0) | CH₃ | 3 | |
| 2-42 | C₆H₅ | (n=0) | C₂H₅ | 3 | $n_D^{22}$ = 1.5675 |
| 2-43 | C₆H₅ | (n=0) | n-C₃H₇ | 3 | |
| 2-44 | C₆H₅ | (n=0) | n-C₄H₉ | 3 | |
| 2-45 | C₆H₅ | (n=0) | n-C₆H₁₃ | 3 | |
| 2-46 | C₆H₅ | (n=0) | n-C₈H₁₇ | 3 | |
| 2-47 | C₆H₅ | (n=0) | n-C₁₀H₂₁ | 3 | |
| 2-48 | C₆H₅-4-CH₃ | (n=0) | CH₃ | 3 | |
| 2-49 | C₆H₅-4-CH₃ | (n=0) | C₂H₅ | 3 | |
| 2-50 | C₆H₅-4-Cl | (n=0) | CH₃ | 3 | |
| 2-51 | C₆H₅-4-Cl | (n=0) | C₂H₅ | 3 | |
| 2-52 | C₆H₅ | (n=0) | CH₂C₆H₅ | 3 | |
| 2-53 | C₆H₅ | (n=0) | CH₂C₆H₄-4-NO₂ | 3 | |
| 2-54 | C₆H₅ | (n=0) | CH₂C₆H₄-4-Cl | 3 | |
| 2-55 | C₆H₅ | (n=0) | CH₂C₆H₄-4-CF₃ | 3 | |

TABLE 3

Structure: F₂C=CH-(CH₂)ₘ-C(=O)-NH-C₆H₄-R₁

| Comp. No. | R₁ | m | Phys. Data |
|---|---|---|---|
| 3-1 | —S(=O)₂N(CH₃)₂ | 9 | 63–65° |
| 3-2 | —S(=O)₂N(H)C₂H₅ | 9 | 46–48° |
| 3-3 | —S(=O)₂N(H)C₃H₇-i | 9 | 116–118° |
| 3-4 | —S(=O)₂C₃H₇-n | 9 | 67–70° |
| 3-5 | —C(=O)CH₃ | 9 | 57–59° |
| 3-6 | -c-C₆H₁₁ | 9 | 94–96° |
| 3-7 | —C(=O)OH | 9 | 214–216° (decompos.) |
| 3-8 | —C(=O)CH₂C₆H₅ | 9 | 125–127° |
| 3-9 | —S(=O)₂N(H)C₂H₅ | 9 | |
| 3-10 | —S(=O)₂N(CH₃)₂ | 3 | |
| 3-11 | —S(=O)₂N(CH₃)₂ | 5 | |
| 3-12 | —S(=O)₂N(CH₃)₂ | 7 | |
| 3-13 | —S(=O)₂C₄H₉-n | 3 | |
| 3-14 | —S(=O)₂OCH₃ | 3 | |
| 3-15 | —S(=O)₂OCH₃ | 9 | |
| 3-16 | —S(=O)₂OC₈H₁₇-n | 3 | |
| 3-17 | —S(=O)₂OC₈H₁₇-n | 9 | |
| 3-18 | —S(=O)₂C₆H₅ | 3 | |
| 3-19 | —S(=O)₂C₆H₅ | 9 | |
| 3-20 | —S(=O)₂OC₆H₅ | 3 | |
| 3-21 | —S(=O)₂O(CH₂)₂OCH₃ | 3 | |
| 3-22 | —S(=O)₂OCH₂C₆H₅ | 3 | |
| 3-23 | —S(=O)₂OCH₂C₆H₅ | 9 | |
| 3-24 | —S(=O)₂O(CH₂)₂OC₆H₅ | 3 | |
| 3-25 | —S(=O)₂OC₁₂H₂₅-n | 3 | |
| 3-26 | —S(=O)₂N(H)C₆H₅ | 3 | |
| 3-27 | —S(=O)₂N(n-C₄H₉)₂ | 3 | |
| 3-28 | —S(=O)₂N(H)C₂H₅ | 3 | |
| 3-29 | —S(=O)₂N(H)C₃H₇-i | 3 | |
| 3-30 | —S(=O)₂N(H)CH₂CH₂OC₂H₅ | 3 | |
| 3-31 | —S(=O)₂-Piperidin-1-yl | 3 | |
| 3-32 | —S(=O)₂-Morpholin-4-yl | 3 | |
| 3-33 | —S(=O)₂-Pyrrolidin-1-yl | 3 | |
| 3-34 | —S(=O)₂N(H)CH₂C₆H₁₁-c | 3 | |
| 3-35 | —S(=O)₂N(H)CH₂C₃H₅-c | 3 | |
| 3-36 | —S(=O)₂N(H)C₃H₅-c | 3 | |
| 3-37 | —S(=O)₂N(H)C₆H₁₁-c | 3 | |
| 3-38 | —S(=O)₂N(H)C₆H₄-4-Cl | 3 | |
| 3-39 | —S(=O)₂N(H)C₆H₄-4-Cl | 9 | |
| 3-40 | —S(=O)₂N(H)C₆H₄-4-CH₃ | 3 | |
| 3-41 | —S(=O)₂N(H)C₆H₄-4-CH₃ | 9 | |
| 3-42 | —S(=O)₂N(H)C₆H₄-4-OCH₃ | 3 | |
| 3-43 | —S(=O)₂N(H)C₆H₄-4-NO₂ | 3 | |
| 3-44 | —S(=O)₂N(H)C₆H₄-4-NO₂ | 9 | |
| 3-45 | —S(=O)₂N(H)C₆H₄-3-CF₃ | 3 | |
| 3-46 | —S(=O)₂N(H)C₆H₄-4-OCF₃ | 3 | |
| 3-47 | —S(=O)₂N(CH₃)C₆H₅ | 3 | |
| 3-48 | —C(=O)C₄H₉-n | 3 | |
| 3-49 | —C(=O)CH₃ | 3 | |
| 3-50 | —C(=O)C₄H₉-n | 9 | |
| 3-51 | —C(=O)C₆H₁₃-n | 3 | |
| 3-52 | —C(=O)C₈H₁₇-n | 3 | |
| 3-53 | —C(=O)C₃H₅-c | 3 | |
| 3-54 | —C(=O)C₆H₁₁-c | 3 | |
| 3-55 | —C(=O)C₆H₁₁-c | 9 | |
| 3-56 | —C(=O)CH₂C₆H₅ | 3 | |
| 3-57 | —C(=O)C₆H₅ | 3 | |
| 3-58 | —C(=O)C₆H₄-4-Cl | 3 | |
| 3-59 | —C(=O)C₆H₄-4-NO₂ | 3 | |
| 3-60 | —C(=O)OH | 3 | |
| 3-61 | -c-C₃H₅ | 3 | |
| 3-62 | -c-C₃H₅ | 9 | |
| 3-63 | —C(=O)N(CH₃)₂ | 3 | |
| 3-64 | —C(=O)N(CH₃)₂ | 9 | |
| 3-65 | —C(=O)N(n-C₄H₉)₂ | 3 | |
| 3-66 | —C(=O)N(n-C₄H₉)₂ | 9 | |
| 3-67 | —C(=O)N(H)C₁₀H₂₁-n | 3 | |

TABLE 3-continued

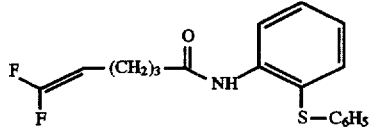

| Comp. No. | R₁ | m | Phys. Data |
|---|---|---|---|
| 3-68 | —C(=O)N(H)C₈H₇-n | 3 | |
| 3-69 | —C(=O)N(H)CH₂CH₂OC₂H₅ | 3 | |
| 3-70 | —C(=O)N(H)CH₂C₆H₅ | 3 | |
| 3-71 | —C(=O)N(H)CH₂C₆H₅ | 9 | |
| 3-72 | —C(=O)N(H)CH₂C₆H₄-4-Cl | 9 | |
| 3-73 | —C(=O)N(H)CH₂C₆H₄-4-CH₃ | 3 | |
| 3-74 | —C(=O)N(H)CH₂C₆H₄-4-CF₃ | 3 | |
| 3-75 | —C(=O)N(H)CH₂C₆H₄-OCH₃ | 3 | |
| 3-76 | —C(=O)N(H)CH₂C₆H₄-3-NO₂ | 3 | |
| 3-77 | —C(=O)N(H)CH₂CH₂C₆H₅ | 3 | |
| 3-78 | —C(=O)N(H)C₆H₅ | 3 | |
| 3-79 | —C(=O)N(H)C₆H₄-4-Cl | 3 | |
| 3-80 | —C(=O)N(H)C₆H₄-4-CH₃ | 3 | |
| 3-81 | —C(=O)N(H)C₆H₃-3,4-(CH₃)₂ | 3 | |
| 3-82 | —C(=O)N(H)C₆H₄-4-C₄H₉-n | 3 | |
| 3-83 | —C(=O)N(H)C₆H₅ | 9 | |
| 3-84 | —C(=O)N(H)C₆H₄-3-CF₃ | 3 | |
| 3-85 | —C(=O)N(H)C₆H₄-4-OCH₃ | 3 | |
| 3-86 | —C(=O)N(H)C₆H₄-4-OC₆H₅ | 3 | |
| 3-87 | —C(=O)N(H)C₆H₄-4-NO₂ | 3 | |
| 3-88 | —C(=O)N(H)C₆H₄-4-NO₂ | 9 | |
| 3-89 | —C(=O)N(H)C₆H₄-4-OCF₃ | 3 | |
| 3-90 | —C(=O)N(H)C₆H₃-3,4-(Cl)₂ | 3 | |
| 3-91 | —C(=O)N(H)CH₂C₃H₅-c | 3 | |
| 3-92 | —C(=O)N(H)CH₂C₆H₁₁-c | 3 | |
| 3-93 | —C(=O)N(H)C₃H₅-c | 3 | |
| 3-94 | —C(=O)N(H)C₆H₁₁-c | 3 | |
| 3-95 | —C(=O)N(H)C₆H₁₁-c | 9 | |
| 3-96 | —C(=O)N(H)C₆H₄-4-CN | 3 | |
| 3-97 | —C(=O)N(H)C₈H₁₅-c | 3 | |
| 3-98 | —C(=O)-Pyrrolidin-1-yl | 3 | |
| 3-99 | —C(=O)-Pyrrolidin-1-yl | 9 | |
| 3-100 | —C(=O)-Piperidin-1-yl | 3 | |
| 3-101 | —C(=O)-Morpholin-4-yl | 3 | |
| 3-102 | —C(=O)-4-CH₃-Piperazin-1-yl | 3 | |
| 3-103 | —C(=O)-1-Azacyclohept-1-yl | 3 | |

TABLE 3-continued

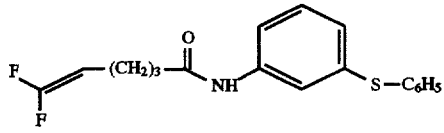

| Comp. No. | R₁ | m | Phys. Data |
|---|---|---|---|
| 3-104 | —C(=O)N(H)CH₂-Pyrid-3-yl | 3 | |
| 3-105 | —C(=O)N(H)CH₂-2-Pyrid-5-yl | 3 | |
| 3-106 | —C(=O)N(H)CH₂-Pyrid-2-yl | 3 | |
| 3-107 | —C(=O)N(H)-Pyrid-2-yl | 3 | |
| 3-108 | —C(=O)N(H)-Pyrid-3-yl | 3 | |
| 3-109 | —C(=O)N(H)-7-Cl-Quinolin-4-yl | 3 | |

TABLE 4

| Compound No. | Formula | Phys. Data |
|---|---|---|

4-1

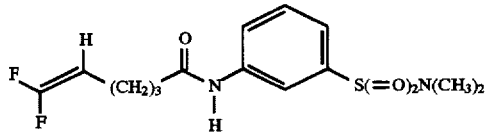

4-2

4-3

TABLE 4-continued

| Compound No. | Formula | Phys. Data |
|---|---|---|
| 4-4 | F₂C=CH-(CH₂)₃-C(=O)-NH-C₆H₄-S(=O)₂N(CH₃)₂ (2-substituted) | |

Formulation Examples (%=per cent by weight)

| Example F1: Emulsion concentrates | a) | b) | c) |
|---|---|---|---|
| Active ingredient No. 1-2 | 25% | 40% | 50% |
| Calcium dodecylbenzene sulfonate | 5% | 8% | 6% |
| Castor oil polyethylene glycol ether (36 mol of EO) | 5% | — | — |
| Tributylphenyl polyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
|---|---|---|---|---|
| Active ingredient No. 1-3 | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidised coconut oil | — | — | 1% | 5% |
| Petroleum spirit (boiling range 160–190° C.) | — | — | 94% | — |

The solutions are suitable for use in the form of microdrops.

| Example F3: Granules | a) | b) | c) | d) |
|---|---|---|---|---|
| Active ingredient No. 1-4 | 5% | 10% | 8% | 21% |
| Kaolin | 94% | — | 79% | 54% |
| Highly-disperse silica | 1% | — | 13% | 7% |
| Attapulgite | — | 90% | — | 18% |

The active ingredient is dissolved in dichloromethane, the solution is sprayed onto the carrier, and the solvent is subsequently evaporated in vacuo.

| Example F4: Dusts | a) | b) |
|---|---|---|
| Active ingredient No. 1-10 | 2% | 5% |
| Highly-disperse silica | 1% | 5% |
| Talc | 97% | — |
| Kaolin | — | 90% |

Ready-to-use dusts are obtained by intimately mixing the carriers with the active ingredient.

| Example F5: Wettable powders | a) | b) | c) |
|---|---|---|---|
| Active ingredient No. 1-1 | 25% | 50% | 75% |
| Sodium ligninsulfonate | 5% | 5% | — |
| Sodium lauryl sulfate | 3% | — | 5% |
| Sodium diisobutylnaphthalene-sulfonate | — | 6% | 10% |
| Octylphenol polyethylene glycol ether (7–8 mol of EO) | — | 2% | — |
| Highly-disperse silica | 5% | 10% | 10% |
| Kaolin | 62% | 27% | — |

The active ingredient is mixed with the additives, and the mixture is ground thoroughly in a suitable mill. This gives wettable powders which can be diluted with water to give suspensions of any desired concentration.

| Example F6: Emulsion concentrate | |
|---|---|
| Active ingredient No. 2-1 | 10% |
| Octylphenol polyethylene glycol ether (4–5 mol of EO) | 3% |
| Calcium dodecylbenzene sulfonate | 3% |
| Castor oil polyglycol ether (36 mol of EO) | 4% |
| Cyclohexanone | 30% |
| Xylene mixture | 50% |

Emulsions of any desired concentration can be prepared from this concentrate by dilution with water.

| Example F7: Dusts | a) | b) |
|---|---|---|
| Active ingredient No. 3-3 | 5% | 8% |
| Talc | 95% | — |
| Kaolin | — | 92% |

Ready-to-use dusts are obtained by mixing the active ingredient with the carrier and grinding the mixture on a suitable mill.

| Example F8: Extruder granules | |
|---|---|
| Active ingredient No. 2-5 | 10% |
| Sodium ligninsulfonate | 2% |
| Carboxymethylcellulose | 1% |
| Kaolin | 87% |

The active ingredient is mixed with the additives, and the mixture is ground and moistened with water. This mixture is extruded, granulated and subsequently dried in a stream of air.

| Example F9: Coated granules | |
| --- | --- |
| Active ingredient No. 2-7 | 3% |
| Polyethylene glycol (MW 200) | 3% |
| Kaolin | 94% |

In a mixer, the finely ground active ingredient is applied uniformly to the polyethylene glycol, which has been moistened with kaolin. Dust-free coated granules are obtained in this manner.

| Example F10: Suspension concentrate | |
| --- | --- |
| Active ingredient No. 3-6 | 40% |
| Ethylene glycol | 10% |
| Nonylphenol polyethylene glycol ether (15 mol of EO) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. This gives a suspension concentrate from which suspensions of any desired concentration can be prepared by dilution with water.

Biological Examples (%=per cent by weight unless otherwise indicated)

Example B1

Action against *Boophilus microplus*

Adult *Boophilus microplus* females that are replete with blood are affixed to a PVC plate and covered with a cotton wool swab. For treatment, 10 ml of an aqueous solution comprising 125 ppm of the test compound are poured over the test insects. The cotton wool swab is then removed and the ticks are incubated for 4 weeks until oviposition has taken place. The action against Boophilus microplus manifests itself either as mortality or sterility of the females or as ovicidal action in the eggs.

In this test, compounds of Tables 1 to 4 exhibit good activity. In particular, compounds nos. 1-1, 1-2, 2-1 and 2-2 are more than 80% effective.

Example B2

Ovicidal action against *Heliothis virescens*

Egg deposits of Heliothis virescens on filter paper are immersed for a short time in an aqueous acetone solution of the test compound having a concentration of 400 ppm. After the test solution has dried, the eggs are incubated in petri dishes. After 6 days, the percentage of eggs that have hatched is evaluated in comparison with untreated controls (% reduction in hatching rate).

In this test, compounds of Tables 1 to 4 exhibit good activity. In particular, compounds nos. 1-1, 1-2, 1-10, 2-1 to 2-6, 2-40, 3-1 to 3-5 and 3-7 are more than 80% effective.

Example B3

Action against *Nilaparvata lugens*

Rice plants are sprayed with an aqueous emulsion comprising 400 ppm of the test compound. After the spray coating has dried, the rice plants are populated with *Nilaparvata lugens* larvae in the 2nd and 3rd stages. Evaluation is made 21 days later. The percentage reduction in the population (% activity) is determined by comparing the number of surviving plant hoppers on the plants with that on untreated plants.

In this test, compounds of Tables 1 to 4 exhibit good activity. In particular, compounds nos. 1-1 to 1-4, 1-10, 2-1 to 2-7, 2-40, 3-1 and 3-4 to 3-8 are more than 80% effective.

Example B4

Action against *Nephotettix cincticeps*

Rice plants are sprayed with an aqueous emulsion comprising 400 ppm of the test compound. After the spray coating has dried, the rice plants are populated with *Nephotettix cincticeps* larvae in the 2nd and 3rd stages. Evaluation is made 21 days later. The percentage reduction in the population (% activity) is determined by comparing the number of surviving leaf hoppers on the treated plants with that on untreated plants.

In this test, compounds of Tables 1 to 4 exhibit good activity. In particular, compounds nos. 1-1 and 2-1 are more than 80% effective.

Example B5

Action against *Bemisia tabaci*

Dwarf bean plants are placed in gauze cages and populated with adults of *Bemisia tabaci* (whitefly). After oviposition has taken place, all adults are removed and 10 days later the plants and the nymphs located thereon are sprayed with an aqueous emulsion of the test compound (concentration 400 ppm). Evaluation is made 14 days after application of the test compound by determining the percentage hatching rate in comparison with untreated controls.

In this test, compounds of Tables 1 to 4 exhibit good activity. In particular, compounds nos. 1-1 to 1-3, 1-10, 2-1 to 2-6, 3-4 and 3-5 are more than 80% effective.

Example B6

Action against *Diabrotica balteata* larvae

Maize seedlings are sprayed with an aqueous emulsion comprising 400 ppm of the test compound. After the spray coating has dried, the maize seedings are populated with 10 *Diabrotica balteata* larvae in the 2nd stage and placed in a plastics container. Evaluation is made 6 days later. The percentage reduction in the population (% activity) is determined by comparing the number of dead larvae on the treated plants with that on untreated plants.

In this test, compounds of Tables 1 to 4 exhibit good activity. In particular, compounds nos. 1-2 to 1-4, 1-10, 2-1, 2-3 to 2-7, 2-40, 2-42, 3-1 and 3-8 are more than 80% effective.

Example B7

Action against *Tetranychus urticae*

Young bean plants are populated with a mixed population of *Tetranychus urticae* and sprayed one day later with an aqueous emulsion comprising 400 ppm of the test compound. The plants are then incubated for 6 days at 25° C. and then evaluated. The percentage reduction in the population (% activity) is determined by comparing the number of dead eggs, larvae and adults on the treated plants with that on untreated plants.

In this test, compounds of Tables 1 to 4 exhibit good activity. In particular, compounds nos. 1-1 to 1-4, 1-10, 2-1 to 2-7, 2-40, 2-42, 3-1 to 3-6 and 3-8 are more than 80% effective.

Example B8

Action against *Heliothis virescens* caterpillars

Young soybean plants are sprayed with an aqueous emulsion comprising the test compound in a concentration of 400 ppm. After the spray coating has dried, each of the soybean plants is populated with 10 caterpillars of *Heliothis virescens* in the first stage and placed in a plastics container. Evaluation is made 6 days later. The percentage reduction in the population and the percentage reduction in feeding damage (% activity) are determined by comparing the number of dead caterpillars and the feeding damage on the treated plants with that on untreated plants.

In this test, compounds of Tables 1 to 4 exhibit good activity. In particular, compounds nos. 1-1 to 1-3, 1-10, 2-1 to 2-6, 2-40, 3-1 and 3-3 to 3-5 are more than 80% effective.

Example B9

Systemic action against *Nilaparvata lugens*

Pots containing rice plants are stood in an aqueous emulsion comprising 400 ppm of test compound. The rice plants are then populated with Nilaparvata lugens larvae in the 2nd and 3rd stages. Evaluation is made 6 days later. The percentage reduction in the population (% activity) is determined by comparing the number of plant hoppers on the treated plants with that on untreated plants.

In this test, compounds of Tables 1 to 4 exhibit good activity. In particular, compounds nos. 1-1 to 1-4, 1-10, 2-1 to 2-7, 2-40 and 3-1 to 3-8 are more than 80% effective.

Example B10

Ovicidal/larvicidal action against *Heliothis virescens*

Egg deposits of *Heliothis virescens* on cotton are sprayed with an aqueous emulsion comprising 400 ppm of test compound 8 days later, the percentage of eggs that have hatched and the survival rate of the caterpillars are evaluated in comparison with untreated controls (% reduction in the population).

In this test, compounds of Tables 1 to 4 exhibit good activity. In particular, compounds nos. 1-1, 1-3, 2-1, 2-2, 2-5, 2-6, 3-1, 3-4 and 3-5 are more than 80% effective.

Example B11

Action against *Panonychus ulmi* (OP and carb. resistant)

Apple seedlings are populated with adult females of *Panonychus ulmi*. After seven days the infested plants are sprayed to drip point with an aqueous emulsion comprising 400 ppm of the test compound and then cultivated in a greenhouse. Evaluation is made 14 days later. The percentage reduction in the population (% activity) is determined by comparing the number of dead spider mites on the treated plants with that on untreated In this test, compounds of Tables 1 to 4 exhibit good activity. In particular, compounds nos. 1-1 to 1-4, 1-10, 2-1 to 2-6 and 3-5 are more than 80% effective.

Example B12

Action against *Dermanyssus gallinae*

2 to 3 ml of a solution comprising 10 ppm of the test compound, and approximately 200 mites (*Dermanyssus gallinae*) at various stages of development, are placed in a glass container that is open at the top. The container is then closed with a cotton wool plug, shaken for 10 minutes until the mites are completely wetted, and then inverted for a short time so that the remaining test solution can be absorbed by the cotton wool. After 3 days, the mortality of the mites is determined as a percentage by counting the number of dead individuals.

In this test, compounds of Tables 1 to 4 exhibit good activity. In particular, compounds nos. 1-1 and 1-2 are more than 80 % effective.

Example B13

Ovicidal action against *Tetranychus urticae*

Young bean plants are populated with *Tetranychus urticae* females which are removed again after 24 hours. The plants having egg deposits are sprayed with an aqueous emulsion comprising 400 ppm of the test compound. The plants are then incubated for 6 days at 25° C. and then evaluated. The percentage reduction in the population (% activity) is determined by comparing the number of dead eggs, larvae and adults on the treated plants with that on untreated plants.

In this test, compounds of Tables 1 to 4 exhibit good activity.

What is claimed is:

1. A compound of formula $$\text{(I)}$$

in which $R_1$ is $C_3$–$C_8$cycloalkyl, halo-$C_3$–$C_8$cycloalkyl, $C_3$–$C_8$cycloalkyl-$C_1$–$C_6$alkyl, halo-$C_3$–$C_8$cycloalkyl-$C_1$–$C_6$alkyl, —S—$R_4$, —$SO_2$—$R_6$ or —CO—$R_9$;

$R_2$ is halogen, $C_1$–$C_4$alkyl or $CF_3$, the substituents $R_2$ being identical or different when n is 2;

$R_4$ is aryl or heteroaryl each of which is unsubstituted or substituted;

$R_6$ is unsubstituted $C_1$–$C_{10}$alkyl, $C_2$–$C_6$alkenyl, $C_2$–$C_6$alkynyl, $C_1$–$C_{20}$alkoxy, $C_2$–$C_6$alkenyloxy, $C_2$–$C_6$-alkynyloxy, $C_1$–$C_4$alkylthio, aryl, aryloxy or arylthio, or substituted $C_1$–$C_{10}$alkyl, $C_2$–$C_6$alkenyl, $C_2$–$C_6$-alkynyl, $C_1$–$C_{20}$alkoxy, $C_2$–$C_6$alkenyloxy, $C_2$–$C_6$alkynyloxy, $C_1$–$C_4$alkylthio, aryl, aryloxy or arylthio, or is —N($R_7$)$R_8$;

$R_7$ and $R_8$ are each independently of the other hydrogen, unsubstituted $C_1$–$C_{20}$alkyl, $C_2$–$C_6$alkenyl, $C_2$–$C_6$alkynyl, $C_3$–$C_8$-cycloalkyl or aryl, or substituted $C_1$–$C_{20}$alkyl, $C_2$–$C_6$alkenyl, $C_2$–$C_6$alkenyl, $C_3$–$C_8$-cycloalkyl or aryl; or $R_7$ and $R_8$ together form $C_4$–$C_6$alkylene, oxa-$C_3$–$C_5$alkylene or aza-$C_3$–$C_5$, alkylene wherein the alkylene, oxa alkylene and aza alkylene groups are unsubstituted or substituted;

$R_9$ is hydroxy, unsubstituted $C_1$–$C_{10}$alkyl, $C_2$–$C_6$alkenyl, $C_2$–$C_6$alkynyl, $C_3$–$C_8$cycloalkyl, aryl or aryloxy, or substituted $C_1$–$C_{10}$alkyl, $C_2$–$C_6$alkenyl, $C_2$–$C_6$alkynyl, $C_3$–$C_8$cycloalkyl, aryl or aryloxy, or is —N($R_{10}$)$R_{11}$;

$R_{10}$ and $R_{11}$ are each independently of the other hydrogen, unsubstituted $C_1$–$C_{20}$alkyl, $C_2$–$C_6$alkenyl, $C_2$–$C_6$alkynyl, $C_3$–$C_8$cycloalkyl, aryl, pyridyl or quinolinyl, or substituted $C_1$–$C_{20}$alkyl, $C_2$–$C_6$alkenyl, $C_2$–$C_6$alkynyl, $C_3$–$C_8$cycloalkyl, aryl, pyridyl or quinolinyl, or $R_{10}$ and $R_{11}$ together form $C_4$–$C_6$alkylene, oxa-$C_3$–$C_5$alkylene or aza-$C_3$–$C_5$alkylene wherein the alkylene, oxaalkylene and azaalkylene groups are unsubstituted or substituted;

$R_{12}$ is hydrogen or unsubstituted or substituted $C_1$–$C_{10}$alkyl;

m is 1, 3, 5, 7, 9 or 11;

n is 0, 1 or 2;

X is fluorine or chlorine; and

Y is hydrogen or methyl, in free form or in salt form.

2. A compound according to claim 1 of formula I, in which $R_1$ is $C_3$–$C_8$cycloalkyl, halo-$C_3$–$C_8$cycloalkyl, $C_3$–$C_8$cycloalkyl-$C_1$–$C_6$alkyl, halo-$C_3$–$C_8$cycloalkyl-$C_1$–$C_6$alkyl, —S—$R_4$, —SO$_2$—$R_6$ or —CO—$R_9$;

$R_2$ is halogen, methyl or CF$_3$, the substituents $R_2$ being identical or different when n is 2;

$R_4$ is aryl or heteroaryl each of which is unsubstituted or substituted;

$R_6$ is unsubstituted $C_1$–$C_{10}$alkyl, $C_2$–$C_6$alkenyl, $C_1$–$C_6$alkoxy, $C_3$–$C_6$alkenyloxy, $C_3$–$C_6$alkynyloxy, $C_1$–$C_4$alkylthio, aryl, aryloxy or arylthio, or substituted $C_1$–$C_{10}$alkyl, $C_2$–$C_6$alkenyl, $C_1$–$C_6$alkoxy, $C_3$–$C_6$alkenyloxy, $C_3$–$C_6$alkynyloxy, $C_1$–$C_4$alkylthio, aryl, aryloxy or arylthio, or is —N($R_7$)$R_8$;

$R_7$ and $R_8$ are each independently of the other hydrogen, unsubstituted $C_1$–$C_{20}$alkyl, $C_2$–$C_6$alkenyl, $C_2$–$C_6$alkynyl, $C_3$–$C_8$cycloalkyl or aryl, or substituted $C_1$–$C_{20}$alkyl, $C_2$–$C_6$alkenyl, $C_2$–$C_6$alkynyl, $C_3$–$C_8$cycloalkyl or aryl; or together form $C_4$–$C_6$alkylene, oxa-$C_3$–$C_5$alkylene or aza-$C_3$–$C_5$alkylene wherein the alkylene, oxaalkylene and azaalkylene groups are unsubstituted or substituted;

$R_9$ is hydroxy, unsubstituted $C_1$–$C_{10}$alkyl, $C_3$–$C_6$alkenyl, $C_3$–$C_6$alkynyl, $C_3$–$C_8$cycloalkyl, aryl or aryloxy, or substituted $C_1$–$C_{10}$alkyl, $C_3$–$C_6$alkenyl, $C_3$–$C_6$alkynyl, $C_3$–$C_8$cycloalkyl, aryl or aryloxy, or is —N($R_{10}$)$R_{11}$;

$R_{10}$ and $R_{11}$ are each independently of the other hydrogen, unsubstituted $C_1$–$C_{10}$alkyl, $C_3$–$C_6$alkenyl, $C_3$–$C_6$alkynyl, $C_3$–$C_8$cycloalkyl, aryl or pyridyl, or substituted $C_1$–$C_{10}$alkyl, $C_3$–$C_6$alkenyl, $C_3$–$C_6$alkynyl, $C_3$–$C_8$cycloalkyl, aryl or pyridyl, or together form $C_4$–$C_6$alkylene, oxa-$C_3$–$C_5$alkylene or aza-$C_3$–$C_5$alkylene wherein the alkylene, oxaalkylene and azaalkylene groups are unsubstituted or substituted;

$R_{12}$ is hydrogen;

m is 1,3,5,7,9 or 11;

n is 0, 1 or 2;

X is fluorine or chlorine; and

Y is hydrogen or methyl.

3. A compound according to claim 1 of formula I in free form.

4. A compound according to claim 3 of formula I, in which $R_1$ is —S—$R_4$ and $R_4$ is aryl which is unsubstituted or substituted by from one to three substituents, selected from the group consisting of halogen, $C_1$–$C_{10}$alkyl, $C_2$–$C_6$alkenyl, $C_2$–$C_6$alkynyl, $C_3$–$C_8$cycloalkyl, halo-$C_1$–$C_6$alkyl, halo-$C_2$–$C_6$alkenyl, halo-$C_2$–$C_6$alkynyl, $C_1$–$C_6$alkoxy, $C_2$–$C_6$alkenyloxy, $C_2$–$C_6$alkynyloxy, halo-$C_1$–$C_6$alkoxy, halo-$C_2$–$C_6$alkenyloxy, halo-$C_2$–$C_6$alkynyloxy, $C_1$–$C_6$alkylthio, halo-$C_1$–$C_{10}$alkylthio, $C_1$–$C_6$alkoxy-$C_1$–$C_6$alkyl, $C_1$–$C_4$alkylsulfinyl, $C_1$–$C_4$alkylsulfonyl, $C_1$–$C_4$alkylsulfinyloxy, $C_1$–$C_4$alkylsulfonyloxy, di-$C_1$–$C_6$alkylamino wherein the alkyl radicals are the same or different, —C(=O)—$R_5$, nitro, $C_1$–$C_2$alkylendioxy, halo-$C_1$–$C_2$alkylendioxy, cyano, and a phenyl, naphthyl, phenoxy, naphthoxy, phenylthio, naphthylthio, phenylsulfonyl, naphthylsulfonyl or pyridyloxy group, which is unsubstituted or mono- or di-substituted by substituents being selected from the group consisting of halogen, $C_1$–$C_4$alkyl and halo-$C_1$–$C_4$alkyl, and $R_5$ is $C_1$–$C_{10}$alkyl, halo-$C_1$–$C_6$alkyl, $C_1$–$C_6$alkoxy, halo-$C_1$–$C_6$alkoxy, $C_3$–$C_6$cycloalkyl, halo-$C_3$–$C_6$cycloalkyl, $C_3$–$C_6$cycloalkyl-$C_1$–$C_3$alkyl or halo-$C_3$–$C_6$cycloalkyl-$C_1$–$C_3$alkyl.

5. A compound according to claim 4 of formula I, in which $R_1$ is —S—$R_4$ and $R_4$ is a phenyl or naphthyl group, which is unsubstituted or substituted by one or two substituents, selected from the group consisting of halogen and $C_1$–$C_4$alkyl.

6. A compound according to claim 3 of formula I, in which $R_1$ is —S—$R_4$ and $R_4$ is heteroaryl, which is unsubstituted or substituted by from one to three substituents, selected from the group consisting of halogen, nitro, $C_1$–$C_4$alkyl, $C_2$–$C_6$alkenyl, $C_2$–$C_6$alkynyl, halo-$C_2$–$C_6$alkenyl, halo-$C_2$–$C_6$alkynyl, $C_3$–$C_8$cycloalkyl, halo-$C_1$–$C_4$alkyl, $C_1$–$C_4$alkoxy, $C_2$–$C_6$alkenyloxy, $C_2$–$C_6$alkynyloxy, halo-$C_1$–$C_4$alkoxy, halo-$C_2$–$C_6$alkenyloxy, halo-$C_2$–$C_6$alkynyloxy, $C_1$–$C_4$alkylthio, halo-$C_1$–$C_4$alkylthio, $C_1$–$C_4$alkylsulfinyl, $C_1$–$C_4$alkylsulfonyl, $C_1$–$C_4$alkylsulfinyloxy, $C_1$–$C_4$alkylsulfonyloxy, $C_1$–$C_4$alkylcarbonyl, $C_1$–$C_4$alkoxycarbonyl and cyano.

7. A compound according to claim 3 of formula I, in which $R_1$ is —SO$_2$—$R_6$ and $R_6$ is $C_1$–$C_{10}$alkyl, $C_2$–$C_6$alkenyl, $C_2$–$C_6$alkynyl, halo-$C_1$–$C_6$alkyl, halo-$C_2$–$C_6$alkenyl, halo-$C_2$–$C_6$alkynyl, $C_1$–$C_{20}$alkoxy, halo-$C_1$–$C_6$alkoxy, $C_1$–$C_6$alkoxy-$C_1$–$C_6$alkyl, $C_1$–$C_6$alkoxy-$C_1$–$C_6$alkoxy, $C_2$–$C_6$alkenyloxy, halo-$C_2$–$C_6$alkenyloxy, $C_2$–$C_6$alkynyloxy, halo-$C_2$–$C_6$alkynyloxy, $C_1$–$C_4$alkylthio, halo-$C_1$–$C_{10}$alkylthio, —N($R_7$)$R_8$, or an aryl, aryloxy, aryl-$C_1$–$C_6$alkyl, aryl-$C_1$–$C_6$alkoxy, aryloxy-$C_1$–$C_6$alkoxy, arylthio or aryloxy-$C_1$–$C_6$alkyl group, wherein the aryl radical is unsubstituted or mono-, di- or tri-substituted, substituents being selected from the group consisting of halogen, $C_1$–$C_4$alkyl, nitro, cyano, $C_1$–$C_4$alkoxy, phenoxy and halo-$C_1$–$C_4$alkyl, and $R_7$ and $R_8$ are each independently of the other hydrogen, $C_1$–$C_{20}$alkyl, $C_2$–$C_6$alkenyl, $C_2$–$C_6$alkynyl, halo-$C_1$–$C_{10}$alkyl, halo-$C_2$–$C_6$alkenyl, halo-$C_2$–$C_6$alkynyl, $C_3$–$C_8$cycloalkyl, halo-$C_3$–$C_8$cycloalkyl, $C_3$–$C_8$cycloalkyl-$C_1$–$C_6$alkyl, $C_1$–$C_6$alkoxy-$C_1$–$C_{10}$alkyl, cyano-$C_1$–$C_6$alkyl, or an aryl, aryl-$C_1$–$C_6$alkyl or aryloxy-$C_1$–$C_6$alkyl group, wherein the aryl radical is unsubstituted or substituted by from one to three substituents, selected from the group consisting of halogen, $C_1$–$C_4$alkyl, nitro, cyano, $C_1$–$C_4$alkoxy, phenoxy, $C_1$–$C_6$alkylcarbonyloxy, halo-$C_1$–$C_4$alkyl and halo-$C_1$–$C_4$alkoxy, or $R_7$ and $R_8$ together form a straight-chained $C_4$–$C_6$alkylene group, a straight-chained oxa-$C_3$–$C_5$alkylene group bonded via carbon, or a straight-chained aza-$C_3$–$C_5$alkylene group bonded via carbon, the alkylene, oxaalkylene or azaalkylene group being unsubstituted or mono- or di-substituted by methyl.

8. A compound according to claim 7 of formula I, in which $R_1$ is —SO$_2$—$R_6$ and $R_6$ is $C_1$–$C_6$alkyl, $C_1$–$C_{20}$alkoxy, $C_1$–$C_4$alkoxy-$C_1$–$C_4$alkoxy or an aryl-$C_1$–$C_4$alkoxy, aryloxy-$C_1$–$C_4$alkoxy, aryl or aryloxy group, in which the aryl group is unsubstituted.

9. A compound according to claim 7 of formula I, in which $R_1$ is —$SO_2$—$R_6$, $R_6$ is —N($R_7$)$R_8$ and $R_7$ and $R_8$ are each independently of the other hydrogen, $C_1$–$C_{20}$alkyl, $C_2$–$C_6$alkenyl, $C_2$–$C_6$alkynyl, halo-$C_1$–$C_{10}$alkyl, halo-$C_2$–$C_6$alkenyl, halo-$C_2$–$C_6$alkynyl, $C_3$–$C_8$cycloalkyl, halo-$C_3$–$C_8$cycloalkyl, $C_3$–$C_8$cycloalkyl-$C_1$–$C_6$alkyl, $C_1C_6$alkoxy -$C_1$–$C_{10}$alkyl, cyano-$C_1$–$C_6$alkyl, or an aryl, aryl-$C_1$–$C_6$alkyl or aryloxy-$C_1$–$C_6$alkyl group, wherein the aryl radical is unsubstituted or substituted by from one to three substituents, selected from the group consisting of halogen, $C_1$–$C_4$alkyl, nitro, cyano, $C_1$–$C_4$alkoxy, phenoxy, $C_1$–$C_6$alkylcarbonyloxy, halo-$C_1$–$C_4$alkyl and halo-$C_1$–$C_4$alkoxy.

10. A compound according to claim 9 of formula I, in which $R_1$ is —$SO_2$—$R_6$, $R_6$ is —N($R_7$)$R_8$ and $R_7$ and $R_8$ are each independently of the other hydrogen or $C_1$–$C_6$alkyl.

11. A compound according to claim 3 of formula I, in which $R_1$ is $C_3$–$C_8$cycloalkyl.

12. A compound according to claim 3 of formula I, in which $R_1$ is —CO—$R_9$ and $R_9$ is hydroxy, $C_1$–$C_{10}$alkyl, halo-$C_1$–$C_{10}$alkyl, $C_1$–$C_6$alkoxy-$C_1$–$C_6$alkyl, $C_2$–$C_6$alkenyl, $C_2$–$C_6$-alkynyl, halo-$C_2$–$C_6$alkenyl, halo-$C_2$–$C_6$alkynyl, $C_3$–$C_8$cycloalkyl, $C_3$–$C_8$cycloalkyl-$C_1$–$C_6$alkyl, halo-$C_3$–$C_8$cycloalkyl, —N($R_{10}$)$R_{11}$, or an aryl, aryloxy, aryl-$C_1$–$C_6$alkyl or aryloxy-$C_1$–$C_4$alkyl group, wherein the aryl radical is unsubstituted or substituted by from one to three substituents, selected from the group consisting of halogen, $C_1$–$C_4$alkyl, halo-$C_1$–$C_4$alkyl, nitro, cyano and $C_1$–$C_4$alkoxy, and $R_{10}$ and $R_{11}$ are each independently of the other hydrogen, $C_1$–$C_{20}$alkyl, $C_2$–$C_6$alkenyl, $C_2$–$C_6$alkynyl, halo-$C_1$–$C_{10}$alkyl, halo-$C_2$–$C_6$alkenyl, halo-$C_2$–$C_6$alkynyl, $C_3$–$C_8$cycloalkyl, halo-$C_3$–$C_8$cycloalkyl, halo-$C_3$–$C_8$cycloalkyl-$C_1$–$C_6$alkyl, $C_3$–$C_8$cycloalkyl-$C_1$–$C_6$alkyl, $C_1$–$C_6$alkoxy-$C_1$–$C_6$alkyl, or an aryl, pyridyl, quinolinyl, aryl-$C_1$–$C_6$alkyl or pyridyl-$C_1$–$C_6$alkyl group, which is unsubstituted or ring-substituted by from one to three substituents, selected from the group consisting of halogen, $C_1$–$C_4$alkyl, halo-$C_1$–$C_4$alkyl, nitro, cyano, $C_1$–$C_4$alkoxy, halo-$C_1$–$C_4$alkoxy and phenoxy, or $R_{10}$ and $R_{11}$ together form a straight-chained $C_4$–$C_6$alkylene group, a straight-chained oxa-$C_3$–$C_5$alkylene group bonded via carbon, or a straight-chained aza-$C_3$–$C_5$alkylene group bonded via carbon, the alkylene, oxaalkylene or azaalkylene group being unsubstituted or mono- or di-substituted by methyl.

13. A compound according to claim 12 of formula I, in which $R_1$ is —CO—$R_9$ and $R_9$ is hydroxy, $C_1$–$C_{10}$alkyl, halo-$C_1$–$C_{10}$alkyl, $C_1$–$C_6$alkoxy-$C_1$–$C_6$alkyl, $C_2$–$C_6$alkenyl, $C_2$–$C_6$-alkynyl, halo-$C_2$–$C_6$alkenyl, halo-$C_2$–$C_6$alkynyl, $C_3$–$C_8$cycloalkyl, $C_3$–$C_8$cycloalkyl-$C_1$–$C_6$alkyl, halo-$C_3$–$C_8$cycloalkyl or an aryl, aryloxy, aryl-$C_1$–$C_6$alkyl or aryloxy-$C_1$–$C_4$alkyl group, wherein the aryl radical is unsubstituted or substituted by from one to three substituents, selected from the group consisting of halogen, $C_1$–$C_4$alkyl, halo-$C_1$–$C_4$alkyl, nitro, cyano and $C_1$–$C_4$alkoxy.

14. A compound according to claim 13 of formula I, in which $R_1$ is —CO—$R_9$ and $R_9$ is hydroxy, $C_1$–$C_{10}$alkyl, $C_3$–$C_8$cycloalkyl or a phenyl or phenyl-$C_1$–$C_4$alkyl group, wherein the phenyl radical is unsubstituted or substituted by 1 or 2 substituents, selected from the group consisting of halogen and nitro.

15. A compound according to claim 3 of formula I, in which $R_1$ is bonded in the 4-position of the phenyl ring shown in formula I.

16. A compound according to claim 3 of formula I, in which n is 0 or 1 and $R_2$ is halogen or $CF_3$.

17. A compound according to claim 3 of formula I, in which m is 3, 7 or 9.

18. A compound according to claim 3 of formula I, in which X is fluorine.

19. A compound according to claim 3 of formula I, in which Y is hydrogen.

20. A compound according to claim 3 of formula I, in which $R_{12}$ is hydrogen or $C_1$–$C_6$-alkyl.

21. A compound according to claim 1 of formula I, selected from the group consisting of the compounds:

(a) 6,6-difluorohex-5-enoic acid N-(4-phenylthiophenyl)amide, (b) 6,6-difluorohex-5-enoic acid N-(4-naphth-2-ylthio phenyl)amide, (c) 6,6-difluorohex-5-enoic acid N-[3-chloro-4-(4-methylphenylthio)phenyl]amide, (d) 6,6-difluorhex-5-enoic acid N-[4-(4-chlorophenylthio)phenyl]amide, (e) 12,12-difluorododec-11-enoic acid N-(4-dimethylaminosulfonyl phenyl)amide, (f) 12,12-difluorododec-11-enoic acid N-(4-ethylaminosulfonyl phenyl)amide and (g) 12,12-difluorododec-11-enoic acid N-(4-propylsulfonyl phenyl)amide.

22. A pesticidal composition which comprises at least one compound as claimed in claim 1 of the formula I, in free form or in agrochemically utilisable salt form, as active ingredient and at least one auxiliary.

23. A composition as claimed in claim 22 for controlling insects or representatives of the order Acarina.

24. A composition as claimed in claim 22 which comprises seed as auxiliary.

25. A process for the preparation of a composition as claimed in claim 22, wherein the active ingredient is mixed intimately and/or ground with the auxiliary(-ies).

26. A method of controlling pests which comprises applying a composition as claimed in claim 22 to the pests or to their environment.

27. A method as claimed in claim 26 for controlling insects or representatives of the order Acarina.

28. A method as claimed in claim 26 for the protection of plant propagation material, which comprises treating the propagation material or the locus where the propagation material is planted.

29. Plant propagation material treated by the method described in claim 28.

* * * * *